(12) United States Patent
Zheng et al.

(10) Patent No.: US 9,743,020 B2
(45) Date of Patent: Aug. 22, 2017

(54) SUPER RESOLUTION OPTOFLUIDIC MICROSCOPES FOR 2D AND 3D IMAGING

(75) Inventors: Guoan Zheng, Pasadena, CA (US);
Changhuei Yang, Pasadena, CA (US);
Samuel Yang, San Dimas, CA (US);
Seung Ah Lee, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 791 days.

(21) Appl. No.: 13/069,651

(22) Filed: Mar. 23, 2011

(65) Prior Publication Data

US 2011/0234757 A1    Sep. 29, 2011

Related U.S. Application Data

(60) Provisional application No. 61/316,762, filed on Mar. 23, 2010.

(51) Int. Cl.
*G01N 15/14* (2006.01)
*G02B 21/36* (2006.01)
(Continued)

(52) U.S. Cl.
CPC ......... *H04N 5/349* (2013.01); *G01N 15/147* (2013.01); *G01N 15/1484* (2013.01); *G02B 21/36* (2013.01); *G06T 3/4053* (2013.01)

(58) Field of Classification Search
USPC ......................................................... 348/46
See application file for complete search history.

(56) References Cited

U.S. PATENT DOCUMENTS

| | | |
|---|---|---|
| 3,736,432 A | 5/1973 | Sweet |
| 4,438,330 A | 3/1984 | Hardy |
| | (Continued) | |

FOREIGN PATENT DOCUMENTS

| | | |
|---|---|---|
| CN | 1588163 A | 3/2005 |
| CN | 101655463 A | 2/2010 |
| | (Continued) | |

OTHER PUBLICATIONS

F.J.Blanco et al "Microfluidic-optical integrated CMOS compatible devices for label-free biochemical sensing," (2006 J. Micromech. Microeng. 16 1006).*

(Continued)

*Primary Examiner* — Mikhail Itskovich
(74) *Attorney, Agent, or Firm* — Sheila Martinez-Lemke; Weaver Austin Villeneuve & Sampson LLP

(57) ABSTRACT

A super resolution optofluidic microscope device comprises a body defining a fluid channel having a longitudinal axis and includes a surface layer proximal the fluid channel. The surface layer has a two-dimensional light detector array configured to receive light passing through the fluid channel and sample a sequence of subpixel shifted projection frames as an object moves through the fluid channel. The super resolution optofluidic microscope device further comprises a processor in electronic communication with the two-dimensional light detector array. The processor is configured to generate a high resolution image of the object using a super resolution algorithm, and based on the sequence of subpixel shifted projection frames and a motion vector of the object.

33 Claims, 12 Drawing Sheets

(51) Int. Cl.
*H04N 5/349* (2011.01)
*G06T 3/40* (2006.01)

(56) References Cited

U.S. PATENT DOCUMENTS

| | | | |
|---|---|---|---|
| 4,692,027 A | 9/1987 | MacGovern et al. | |
| 4,737,621 A | 4/1988 | Gonsiorowski et al. | |
| 4,981,362 A | 1/1991 | DeJong et al. | |
| 5,196,350 A | 3/1993 | Backman et al. | |
| 5,225,057 A | 7/1993 | LeFebvre et al. | |
| 5,349,191 A | 9/1994 | Rogers | |
| 5,362,653 A | 11/1994 | Carr et al. | |
| 5,420,959 A | 5/1995 | Walker et al. | |
| 5,495,337 A | 2/1996 | Goshorn et al. | |
| 5,545,561 A | 8/1996 | Lleonart Aliberas | |
| 5,684,906 A | 11/1997 | Sugawara | |
| 5,795,755 A | 8/1998 | Lemelson | |
| 5,796,112 A | 8/1998 | Ichie | |
| 5,798,262 A | 8/1998 | Garini et al. | |
| 5,892,577 A | 4/1999 | Gordon | |
| 5,973,316 A | 10/1999 | Ebbesen et al. | |
| 6,058,209 A | 5/2000 | Vaidyanathan et al. | |
| 6,143,247 A | 11/2000 | Sheppard, Jr. et al. | |
| 6,147,798 A | 11/2000 | Brooker et al. | |
| 6,194,718 B1 | 2/2001 | Dotan | |
| 6,215,114 B1 | 4/2001 | Yagi et al. | |
| 6,499,499 B2 | 12/2002 | Dantsker et al. | |
| 6,519,313 B2 | 2/2003 | Venkataramani et al. | |
| 6,555,816 B1 | 4/2003 | Sawahata et al. | |
| 6,608,717 B1 | 8/2003 | Medford et al. | |
| 6,717,726 B2 | 4/2004 | Boehm et al. | |
| 6,753,131 B1 | 6/2004 | Rogers et al. | |
| 6,784,417 B2 | 8/2004 | Sonoki | |
| 6,858,436 B2 | 2/2005 | Zenhausern et al. | |
| 6,903,820 B2 | 6/2005 | Wang | |
| 6,937,323 B2 | 8/2005 | Worthington et al. | |
| 6,944,322 B2 * | 9/2005 | Johnson et al. | 382/128 |
| 7,005,654 B2 | 2/2006 | Seyfried | |
| 7,045,781 B2 | 5/2006 | Adamec et al. | |
| 7,133,130 B2 | 11/2006 | Storz et al. | |
| 7,142,296 B2 | 11/2006 | Cunningham et al. | |
| 7,250,598 B2 | 7/2007 | Hollingsworth et al. | |
| 7,253,947 B2 | 8/2007 | Bromage et al. | |
| 7,271,885 B2 | 9/2007 | Schermer | |
| 7,283,229 B2 | 10/2007 | Noguchi et al. | |
| 7,323,681 B1 | 1/2008 | Oldham et al. | |
| 7,369,234 B2 | 5/2008 | Beaglehole | |
| 7,418,118 B2 | 8/2008 | Furnas et al. | |
| 7,641,856 B2 | 1/2010 | Padmanabhan et al. | |
| 7,671,987 B2 | 3/2010 | Padmanabhan et al. | |
| 7,692,773 B2 | 4/2010 | Roth | |
| 7,705,331 B1 | 4/2010 | Kirk et al. | |
| 7,738,695 B2 | 6/2010 | Shorte et al. | |
| 7,751,048 B2 | 7/2010 | Yang et al. | |
| 7,768,654 B2 | 8/2010 | Cui et al. | |
| 7,773,227 B2 | 8/2010 | Yang et al. | |
| 7,776,586 B2 | 8/2010 | Cregan et al. | |
| 7,892,168 B2 | 2/2011 | Sano | |
| 7,986,824 B2 | 7/2011 | Suzuki et al. | |
| 8,139,106 B2 | 3/2012 | Maiya | |
| 8,314,933 B2 | 11/2012 | Cui et al. | |
| 8,325,349 B2 | 12/2012 | Cui et al. | |
| 8,337,786 B2 | 12/2012 | McLellan et al. | |
| 8,345,351 B2 | 1/2013 | Takeuchi | |
| 8,355,133 B2 | 1/2013 | Dultz et al. | |
| 8,490,469 B2 | 7/2013 | Superfine et al. | |
| 8,498,681 B2 | 7/2013 | Wang et al. | |
| 8,501,435 B2 | 8/2013 | Gustafsson et al. | |
| 8,526,006 B2 | 9/2013 | Nebosis et al. | |
| 8,624,968 B1 | 1/2014 | Hersee et al. | |
| 8,730,574 B2 | 5/2014 | Araya et al. | |
| 8,837,045 B2 | 9/2014 | Popescu et al. | |
| 8,855,265 B2 | 10/2014 | Engel et al. | |
| 8,866,063 B2 | 10/2014 | Ozcan et al. | |
| 8,928,890 B2 | 1/2015 | Nebosis et al. | |
| 8,946,619 B2 | 2/2015 | Wu et al. | |
| 8,964,017 B2 | 2/2015 | Vertikov et al. | |
| 8,970,671 B2 | 3/2015 | Pavani et al. | |
| 8,993,961 B2 | 3/2015 | Tsuneta et al. | |
| 9,105,102 B1 | 8/2015 | Walther et al. | |
| 9,280,707 B2 | 3/2016 | Ishihara | |
| 9,291,998 B2 | 3/2016 | Huys et al. | |
| 9,333,503 B2 | 5/2016 | Zantl et al. | |
| 9,343,494 B2 | 5/2016 | Lee et al. | |
| 9,426,429 B2 | 8/2016 | Zheng et al. | |
| 2002/0070350 A1 | 6/2002 | Rushbrooke et al. | |
| 2002/0080240 A1 | 6/2002 | Omi | |
| 2003/0012277 A1* | 1/2003 | Azuma et al. | 375/240.08 |
| 2003/0032039 A1 | 2/2003 | Cunningham et al. | |
| 2003/0142291 A1 | 7/2003 | Padmanabhan et al. | |
| 2003/0174992 A1 | 9/2003 | Levene et al. | |
| 2003/0203502 A1 | 10/2003 | Zenhausern et al. | |
| 2004/0135079 A1 | 7/2004 | Moellmann | |
| 2004/0146965 A1 | 7/2004 | Brayton | |
| 2004/0156610 A1 | 8/2004 | Charlton et al. | |
| 2004/0175734 A1 | 9/2004 | Stahler et al. | |
| 2004/0224380 A1 | 11/2004 | Chou et al. | |
| 2004/0264637 A1 | 12/2004 | Wang | |
| 2005/0013478 A1 | 1/2005 | Oba et al. | |
| 2005/0078362 A1 | 4/2005 | Borlinghaus | |
| 2005/0271548 A1 | 12/2005 | Yang et al. | |
| 2006/0003145 A1 | 1/2006 | Hansen et al. | |
| 2006/0007436 A1 | 1/2006 | Kurosawa et al. | |
| 2006/0013031 A1 | 1/2006 | Ravkin et al. | |
| 2006/0077535 A1 | 4/2006 | Luther et al. | |
| 2006/0092503 A1 | 5/2006 | Saunders | |
| 2006/0124870 A1 | 6/2006 | Bobanovic et al. | |
| 2006/0175528 A1 | 8/2006 | Greenaway et al. | |
| 2006/0227328 A1 | 10/2006 | Vanwiggeren et al. | |
| 2007/0046924 A1 | 3/2007 | Chang | |
| 2007/0052953 A1 | 3/2007 | Hill | |
| 2007/0058054 A1 | 3/2007 | Kagayama et al. | |
| 2007/0081200 A1 | 4/2007 | Zomet et al. | |
| 2007/0207061 A1 | 9/2007 | Yang et al. | |
| 2007/0229852 A1 | 10/2007 | Wack et al. | |
| 2007/0236782 A1 | 10/2007 | Sano | |
| 2007/0258096 A1 | 11/2007 | Cui et al. | |
| 2008/0056610 A1 | 3/2008 | Kanda | |
| 2008/0144029 A1 | 6/2008 | Li | |
| 2008/0158566 A1 | 7/2008 | Suzuki et al. | |
| 2008/0174862 A1 | 7/2008 | Focht | |
| 2008/0204551 A1 | 8/2008 | O'Connell et al. | |
| 2008/0213141 A1* | 9/2008 | Pinchot | 422/193 |
| 2008/0214412 A1 | 9/2008 | Stahler et al. | |
| 2008/0259345 A1 | 10/2008 | Fukutake | |
| 2009/0086314 A1 | 4/2009 | Namba et al. | |
| 2009/0091811 A1 | 4/2009 | Asundi et al. | |
| 2009/0122070 A1 | 5/2009 | Aragaki et al. | |
| 2009/0166518 A1 | 7/2009 | Tay et al. | |
| 2009/0180179 A1 | 7/2009 | Ryu | |
| 2009/0225309 A1 | 9/2009 | Demou | |
| 2009/0225319 A1 | 9/2009 | Lee et al. | |
| 2009/0237502 A1 | 9/2009 | Maiya | |
| 2009/0268280 A1 | 10/2009 | Osawa et al. | |
| 2009/0273829 A1 | 11/2009 | Terakawa et al. | |
| 2009/0276188 A1 | 11/2009 | Cui et al. | |
| 2010/0033561 A1 | 2/2010 | Hersee | |
| 2010/0045955 A1 | 2/2010 | Vladimirsky et al. | |
| 2010/0108873 A1 | 5/2010 | Schwertner | |
| 2010/0290049 A1 | 11/2010 | Yang et al. | |
| 2010/0296094 A1 | 11/2010 | Yang et al. | |
| 2010/0308427 A1 | 12/2010 | Lenchenkov | |
| 2011/0001815 A1 | 1/2011 | Nakano et al. | |
| 2011/0063592 A1 | 3/2011 | Ezura et al. | |
| 2011/0069382 A1 | 3/2011 | Toomre et al. | |
| 2011/0098950 A1 | 4/2011 | Carr | |
| 2011/0102888 A1 | 5/2011 | Honda et al. | |
| 2011/0170105 A1 | 7/2011 | Cui et al. | |
| 2011/0181884 A1 | 7/2011 | Cui et al. | |
| 2011/0266181 A1 | 11/2011 | Morozov | |
| 2012/0086995 A1 | 4/2012 | Gerchberg et al. | |
| 2012/0098950 A1 | 4/2012 | Zheng et al. | |
| 2012/0099803 A1 | 4/2012 | Ozcan et al. | |
| 2012/0157160 A1 | 6/2012 | Ozcan et al. | |

(56) References Cited

U.S. PATENT DOCUMENTS

| | | | |
|---|---|---|---|
| 2012/0218379 | A1 | 8/2012 | Ozcan et al. |
| 2012/0223214 | A1 | 9/2012 | Lee et al. |
| 2012/0223217 | A1 | 9/2012 | Zheng et al. |
| 2012/0228475 | A1 | 9/2012 | Pang et al. |
| 2012/0248292 | A1 | 10/2012 | Ozcan et al. |
| 2012/0258525 | A1 | 10/2012 | Iizumi et al. |
| 2012/0275681 | A1 | 11/2012 | Honda et al. |
| 2014/0133702 | A1 | 5/2014 | Zheng et al. |

FOREIGN PATENT DOCUMENTS

| | | |
|---|---|---|
| DE | 202 14 835 U1 | 1/2003 |
| EP | 1 371 965 | 12/2003 |
| EP | 1 635 692 | 3/2006 |
| EP | 1 787 156 | 5/2007 |
| EP | 1 956 360 | 8/2008 |
| FR | 2 602 241 | 2/1988 |
| JP | 2003-207454 A | 7/2003 |
| JP | 2003-0524779 A | 8/2003 |
| JP | 2004-505272 A | 2/2004 |
| JP | 2010-020151 A | 1/2010 |
| JP | 2013-542468 A | 11/2013 |
| JP | 2014-515179 A | 6/2014 |
| WO | WO 91/09300 | 6/1991 |
| WO | WO 02/10713 A2 | 2/2002 |
| WO | WO 2004/038484 | 5/2004 |
| WO | WO 2005/121749 | 12/2005 |
| WO | WO 2008/112416 | 9/2008 |
| WO | WO 2009/111573 | 9/2009 |
| WO | WO 2009/111577 | 9/2009 |
| WO | WO 2009/113544 | 9/2009 |
| WO | WO 2010/141702 | 12/2010 |
| WO | WO 2011/119678 | 9/2011 |
| WO | WO 2011/139641 | 11/2011 |
| WO | WO 2012/058233 | 5/2012 |
| WO | WO 2012/094523 | 7/2012 |
| WO | WO 2012/119094 | 9/2012 |
| WO | WO 2012/119114 | 9/2012 |

OTHER PUBLICATIONS

United States Patent and Trademark Office (USPTO) Office Action in U.S. Appl. No. 11/125,718 dated on Nov. 14, 2008.
United States Patent and Trademark Office (USPTO) Final Office Action in U.S. Appl. No. 11/125,718 dated on Jul. 1, 2009.
United States Patent and Trademark Office (USPTO) Notice of Allowance in U.S. Appl. No. 11/125,718 dated on Mar. 11, 2010.
United States Patent and Trademark Office (USPTO) Office Action in U.S. Appl. No. 12/797,132 dated on Oct. 15, 2010.
United States Patent and Trademark Office (USPTO) Office Action in Patent Application U.S. Appl. No. 11/686,095 dated on Jan. 10, 2008.
United States Patent and Trademark Office (USPTO) Office Action in U.S. Appl. No. 11/686,095 dated on Jul. 17, 2008.
United States Patent and Trademark Office (USPTO) Office Action in U.S. Appl. No. 11/686,095 dated on Feb. 26, 2009.
United States Patent and Trademark Office (USPTO) Final Office Action in U.S. Appl. No. 11/686,095 dated on Oct. 28, 2009.
United States Patent and Trademark Office (USPTO) Notice of Allowance in U.S. Appl. No. 11/686,095 dated on Feb. 25, 2010.
United States Patent and Trademark Office (USPTO) Office Action in U.S. Appl. No. 12/785,635 dated on Oct. 15, 2010.
United States Patent and Trademark Office (USPTO) Restriction Requirement in U.S. Appl. No. 12/398,050 dated on Aug. 10, 2011.
United States Patent and Trademark Office (USPTO) Office Action in U.S. Appl. No. 12/398,050 dated on Nov. 14, 2011.
United States Patent and Trademark Office (USPTO) Notice of Allowance in U.S. Appl. No. 12/398,050 dated on Jul. 17, 2012.
United States Patent and Trademark Office (USPTO) Notice of Allowance in U.S. Appl. No. 12/398,050 dated on Aug. 28, 2012.
United States Patent and Trademark Office (USPTO) Office Action in U.S. Appl. No. 12/398,098 dated on May 25, 2011.
United States Patent and Trademark Office (USPTO) Final Office Action in U.S. Appl. No. 12/398,098 dated on Nov. 23, 2012.
United States Patent and Trademark Office (USPTO) Office Action in U.S. Appl. No. 12/398,098 dated on Jul. 1, 2013.
United States Patent and Trademark Office (USPTO) Final Office Action in U.S. Appl. No. 12/398,098 dated on Mar. 27, 2014.
United States Patent and Trademark Office (USPTO) Non-Final Office Action in U.S. Appl. No. 13/281,287 dated on Oct. 31, 2013.
United States Patent and Trademark Office (USPTO) Final Office Action in U.S. Appl. No. 13/281,287 dated on Mar. 12, 2014.
United States Patent and Trademark Office (USPTO) Non-Final Office Action in U.S. Appl. No. 13/411,103 dated on Mar. 11, 2014.
PCT International Search Report dated Oct. 16, 2006 issued in PCT/US2005/016876.
PCT Written Opinion dated Oct. 16, 2006 issued in PCT/US2005/016876.
PCT International Preliminary Report on Patentability dated Dec. 4, 2006 issued in PCT/US2005/016876.
European Patent Office (EPO) European Supplementary Search Report dated Jan. 26, 2012 issued in EP Application No. 05 74 9488.2.
European Patent Office (EPO) Office Action dated Jun. 27, 2012 issued in EP Patent Application No. 05 749 488.2.
Japanese Patent Office (JPO) Office Action dated Jul. 26, 2011 issued in JPO patent Application No. 2007-515164.
Japanese Patent Office (JPO) Office Action dated May 8, 2012 issued in JPO patent Application No. 2007-515164.
PCT International Search Report dated Aug. 26, 2008 issued in PCT/US2008/054908.
PCT Written Opinion dated Aug. 26, 2008 issued in PCT/US2008/054908.
PCT International Preliminary Report on Patentability dated Sep. 15, 2009 issued in PCT/US2008/054908.
European Patent Office (EPO) European Supplementary Search Report dated Feb. 7, 2012 issued in EP Patent Application No. 08 730 664.3.
European Patent Office (EPO) Office Action dated Jun. 12, 2014 issued in EP Patent Application No. 08 730 664.3.
Japanese Patent Office (JPO) Office Action Jan. 24, 2012 issued in JPO patent Application No. 2009-553675.
PCT International Search Report dated Apr. 23, 2009 issued in PCT/US2009/036045.
PCT Written Opinion dated Apr. 23, 2009 issued in PCT/US2009/036045.
PCT International Preliminary Report on Patentability and Written Opinion dated Sep. 16, 2010 issued in PCT/US2009/036045.
European Search Report dated Feb. 11, 2013 issued in EP 09 716 850.4.
PCT International Search Report dated Jun. 29, 2009 issued in PCT/2009/036052.
PCT Written Opinion dated Jun. 29, 2009 issued in PCT/2009/036052.
PCT International Preliminary Report on Patentability and Written Opinion dated Sep. 16, 2010 issued in PCT/2009/036052.
PCT International Search Report dated Dec. 7, 2011 issued in PCT/US2011/029542.
PCT International Preliminary Report on Patentability and Written Opinion dated Oct. 4, 2012 issued in PCT/US2011/029542.
Chinese First Office Action dated Jan. 23, 2014 issued in CN 201180012251.6.
European Search Report dated Jun. 25, 2014 issued in EP 11 760 112.0.
PCT International Search Report dated May 8, 2012 issued in PCT/US2011/057735.
PCT International Preliminary Report on Patentability and Written Opinion dated May 10, 2013 issued in PCT/US2011/057735.
European Search Report dated Jun. 25, 2014 issued in EP 11 836 959.
European Office Action dated Jul. 3, 2014 issued in EP 11 836 959.4.

(56) References Cited

OTHER PUBLICATIONS

PCT International Search Report and Written Opinion dated Sep. 25, 2012 issued in PCT/US2012/027575.
PCT International Preliminary Report on Patentability and Written Opinion dated Sep. 12, 2013 issued in PCT/US2012/027575.
European Search Report dated Jun. 25, 2014 issued in EP 12 75 2493.
PCT International Search Report and Written Opinion dated Sep. 21, 2012 issued in PCT/US2012/027522.
PCT International Preliminary Report on Patentability and Written Opinion dated Sep. 12, 2013 issued in PCT/US2012/027522.
European Supplementary Search Report dated Jun. 25, 2014 issued in EP 12 75 2808.
Confocal Raman Microscopy (Oct. 2006) "Optofluidic Microscope Enables Lensless Imaging of Microorganisms," *Biophotonics International*, 13(10):24.
Adams, Mark L.,et al., (2003) "Microfluidic Integration on detector arrays for absorption and fluorescence micro-spectrometers," *Sensors and Actuators A*, 104:25-31.
Baker et al., (2003) "Molecular Detection of Breast Cancer Cells in the Peripheral Blood of Advanced-Stage Breast Cancer Patients Using Multimarker Real-Time Reverse Transcription-Polymerase Chain Reaction and a Novel Porous Barrier Density Gradient Centrifugation Technology," *Clinical Cancer Research* 9:4865-4871.
Beebe, David J., et al., (2002) "Physics and Applications of Microfluidics in Biology," *Annu. Rev. Biomed., Eng.*, 4:261-286.
Bethe, H.A., (1944) "Theory of Diffraction by Small Holes," *The Physical Review*, 66(7-8):163-182.
Biddiss, Elaine, et al., (2004) "Hetergeneous Surface Charge Enhanced Micromixing for Electrokinetic Flows," *Anal. Chem.*, 76:3208-3213.
Bishara et al., (May 24, 2010) "Lensfree on-chip microscopy over a wide field-of-view using pixel super-resolution," opticsinfobase. org, *Opt. Expr.* 18(11):11181-11191.
Boppart, S. A., et al., (1997) "Forward-imaging instruments for optical coherence tomography," *Optics Letters*, 22:1618-1620.
Bourzac, (Jul. 30, 2008) "Tiny $10 Microscope, a high-resolution, lens-free microscope fits on a dime-size chip," *Technology Review*, 2 pp.
Braun et al., (2005) "Circulating and Disseminated Tumor Cells," *Journal of Clinical Oncology*, 23:1623-1626.
Buley (Feb. 6, 2009) The $10 Microscope, by Taylor, Forbes.com, LLC., 2 pp.
Bullock, (Oct. 13, 2008) "Microscope-On-a-Chip Is One Step Closer to the Tricorder," *Wired*, 8 pp.
Cai et al., (Mar. 24, 2004) "Insulinoma-Associated Protein IA-2, a Vesicle Transmembrane Protein, Genetically Interacts with UNC-31/CAPS and Affects Neurosecretion in *Caenorhabditis elegans*," *The Journal of Neuroscience*, 24(12):3115-3124.
Cao, Jinhua, et al., (2004) "Brownian Particle Distribution in Tube Flows," *Proceedings of IMECE04*, 260:243-252.
Chovin, Arnaud, et al., (2004) "Fabrication, Characterization, and Far-Field Optical Properties of an Ordered Array of Nanoapertures," *Nano Letters*, 4(10):1965-68.
Collet et al., (Jan. 1998) "Analysis of *osm*-6 That Affects Sensory Cilium Structure and Sensory Neuron Function in *Caenorhabditis elegans*," *Genetics*, 148:187-200.
Conrad et al. (2004) "Automatic Identification of Subcellular Phenotypes on Human Cell Arrays," *Genome Research*, www.genome. org, 14:1130-1136.
Cote, et al. (1988) "Monoclonal-Antibodies Detect Occult Breast-Carcinoma Mestastases in the Bone-Marrow of Patients with Early Stage Disease," *American Journal of Surgical Pathology* 12:333-340.
Cote, et al. (1991) "Prediction of Early Relapse in Patients with Operable Breast-Cancer by Detection of Occult Bone-Marrow Micrometastases," *Journal of Clinical Oncology*, 9:1749-1756.
Courjon, Daniel, (2003) "Near-field Microscopy and near-field optics," *Imperial College Press*, 317 pages.

Cristofanilli et al., (2004) "Circulating Tumor Cells, Disease Progression, and Survival in Metastatic Breast Cancer," *New England Journal of Medicine*, 351:781-791.
Cui, X. et al., (Jan. 2006) "Portable Optical microscope-on-a-chip," *Photonics West*, San Jose, CA, 8pp.
Cui, Xiquan, et al., (Aug. 5, 2008) "Lensless high-resolution on-chip optofluidic microscopes for *Caenorhabditis elegans* and cell imaging," *Proceedings of the National Academy of Sciences of the United States of America*, 105(31):10670-10675.
Cui, Xiquan, et al., (2008) "Quantitative differential interference contrast microscopy based on structured-aperture interference," *Applied Physics Letters*, 93:091113-1-091113-3.
Cui, Xiquan, et al., (2006) "Slanted hole array beam profiler (SHArP)—a high-resolution portable beam profiler based on a linear aperture array," *Optics Letters*, 31(21):3161-3163.
Dahan, M., et al., (2001) "Time-gated biological imaging by use of colloidal quantum dots," *Optics Letters*, 26(11):825-827.
Dearnaley, et al. (1983) "Detection of Isolated Mammary-Carcinoma Cells in Marrow of Patients with Primary Breast-Cancer," *Journal of Royal Society of Medicine*, 76:359-364.
De Fornel, F., (2001) "Evanescent waves from Newtonian optics and Atomic optics," *Springer Series in Optical Sciences*, 270 pages.
Diel et al., (1996) "Micrometastatic breast cancer cells in bone marrow at primary surgery: Prognostic value in comparison with nodal," *Journal of the National Cancer Institute*, 88:1652-1658.
Doyle, P. S., et al., (Mar. 2002) "Self-assembled magnetic matrices for DNA separation chips," *Science*, 295(5563):2237.
Elad, M., and Hel-Or, Y., (Dec. 1998) "A Fast Super-Resolution Reconstruction Algorithm for Pure Translational Motion and Common Space-Invariant Blur," *IEEE Transactions on Image Processing*, 10:1187-1193.
Erickson et al., (Feb. 2008) "OPTOFLUIDICS: Emerges from the Laboratory," *Photonics Spectra*, pp. 74-79.
Farsiu, S. et al., (Jan. 2004) "Advances and challenges in super-resolution," *Wiley Periodicals*, 14:47-57.
Farsiu, S., et al., (Oct. 2004) "Fast and robust multiframe super resolution," *IEEE Transactions on Image Processing*, 13(10):1327-1344.
Fountain, (Jul. 29, 2008) "Bringing Microscopes Down to Size in Quest for More Compact Labs," *New York Times*, 1 page.
Furtado et al., (2002) "Measurement of green fluorescent protein concentration in single cells by image analysis," *Analytical Biochemistry*, 310:84-92.
Gillette, J., et al., (1995) "Aliasing reduction in staring infrared imagers utilizing subpixel techniques," *Optical Engineering*, 34:3130.
Hardie Russell C., et al., (Apr. 1997) "High resolution image reconstruction from a sequence of rotated and translated frames and its application to an infrared imaging system," *Optical Engineering*, 27 pp.
Hayden, (Jun. 4, 2009) "Microscopic marvels: Microscope for the masses," *Nature* 459(7247):632-633.
Hedgecock et al., (1985) "Axonal Guidance Mutants of *Caenorhabditis elegans* Identified by Filling Sensory Neurons with Fluorescein Dyes," *Developmental Biology*, 111:158-170.
Heng, Xin, (Apr. 1, 2005) "OptoFuidic Microscopy (OFM)" *Biophotonics Group, Caltech, DARPA optofluidic center retreat*, 9pp.
Heng, Xin, et al., (2006) "Characterization of light collection through a subwavelength aperture from a point source," *Optics Express*, 14:10410-10425.
Heng, Xin, et al., (2006) "Optofluidic Microscopy—a method for implementing a high resolution optical microscope on a chip," *Lab Chip*, 6(10):1274-1276.
Heng, Xin, et al., (Jul. 17, 2006) "Optofluidic Microscopy: A Novel High Resolution Microscope-on-a-Chip System," *Leos Summer Topical Meetings, 2006 Digest of the Quebec City*, QC, Canada Jul. 17-19, 2006, Piscataway, NJ, USA, IEEE, 6(10):15-16.
Heng, Xin, et al., (2007) "An Optical Tweezer Actuated, Nanoaperture-grid based Optofluidic Microscope Implimentation Method," Optics Express, 15(25):16367-75.
Hogan, (Feb. 2008) "Gaining High Resolution with Nanoaperture Grid," *Photonics Spectra*, p. 103.

(56) References Cited

OTHER PUBLICATIONS

Hogan, (Jul. 2008) "Getting in Deeper," *Biophotonics*, p. 25 (5 pages).

Jaiswal, Jyoti K., et al., (2003) "Long-term multiple color imaging of live cells using quantum dot biconjugates," *Nature Biotechnology*, 21:47-51.

Jung et al. (2003) "Clinical Significance of Bone Marrow Micrometastasis Detected by Nested RT-PCR for Keratin-19 in Breast Cancer Patients," *Japanese Journal of Clinical Oncology*, 33:167-172.

Kapur, J., et al., (1985) "A New Method for Gray-Level Picture Thresholding Using the Entropy of the Histogram," *Computer vision, graphics, and image processing*, 29:273-285.

Kim et al., (2001) "Detection of Breast Cancer Micrometastases in Peripheral Blood Using Immunomagnetic Separation and Immunocytochemistry," *Breast Cancer*, 8:63-69.

Lechevallier et al., (Sep. 1991) "Occurrence of Giardia and *Cryptosporidium* spp. In surface water supplies," *Appl. Environ. Microbiol.*, 57(9):2610-2616.

Lange et al., (2005) "A microfluidic shadow imaging system for the study of the nematode *Caenorhabditis elegans* in space," *Sensors and Actuators B*, 107:904-914.

Lara et al., (2004) "Enrichment of Rare Cancer Cells Through Depletion of Normal Cells Using Density and Flow-Through, Immunomagnetic Cell Separation," *Experimental Hematology* 32:891-904.

Lay, Christophe, et al., "Enhanced microfiltration devices configured with hydrodynamic trapping and a rain drop bypass filtering architecture for microbial cells detection," *Lab on a Chip* 2008, 8:830-833; published as Advanced Article on Apr. 1, 2008 at http://pubs.rsc.org | DOI:10.1039/b800015h, 4 pp.

Lee, Lap Man, et al., (2009) "The Application of On-Chip Optofluidic Microscopy for Imaging *Giardia lamblia* Trophozoites and Cysts," *Biomed Microdevices*, Springer DOI 10.1007/s10544-009-9312-X 11:951-958.

Lee, Seung Ah, et al., (Oct. 2011) "Color Capable Sub-Pixel Resolving Optofluidic Microscope and Its Application to Blood Cell Imaging for Malaria Diagnosis," *PLoS One* 6(10):e26127, 6 pages.

Lee, Seung, Ah, et al., (Mar. 20, 2012) "On-chip continuous monitoring of motile microorganisms on an ePetri platform," *Lab on a Chip* 12(13):2385-2390.

Leonard (Oct. 2008) "Microscope-on-a-Chip Is Small in Size, Big in Scope," *Medical Manufacturing News*, 1 page.

Lew, Matthew et al., (Oct. 15, 2007) "Interference of a four-hole aperture for on-chip quantitative two-dimensional differential phase imaging," *Optic Letters*, 32(20):2963-2965.

Lezec, H.J., and Thio, T., (Aug. 2004) "Diffracted evanescent wave model for enhanced and suppressed optical transmission through subwavelength hole arrays," *Optics Express*, 12(16):3629-3651.

Li et al., (1997) "Transport, Manipulation, and Reaction of Biological Cells On-Chip Using Electrokinetic Effects," *Anal. Chem*, 69:1564-1568.

Liang, J. Z., et al., (Nov. 1997) "Supernormal vision and high-resolution retinal imaging through adaptive optics," *Journal of the Optical Society of America*, 14(11):2884-2892.

Lin, Z., and Shum, H.-Y., (2004) "Fundamental limits of reconstruction-based superresolution algorithms under local translation," *IEEE Transactions on Pattern Analysis and Machine Intelligence*, pp. 83-97.

Liu and Yang (Aug. 16, 2012) "Themed issue: Optofluidics," *Editorial, Lab on a Chip* 12(19): 3539-3539.

Liu and Yang (May 30, 2013) "Optofluidics 2013," *Editorial, Lab on a Chip Advance Article*, Downloaded on Nov. 6, 2013, RSC Publishing, 2 pages.

Lugo et al., (2003) "Detection and Measurement of Occult Disease for the Prognosis of Solid Tumors," *Journal of Clinical Oncology*, 21:2609-2615.

Madrigal, (Jul. 28, 2008) "Mini-Microscope Could Lead to Cell-Sorting Implants," downloaded from http:www.wired.com/wiredscience/2008/07/mini-microscope, 3 pp.

Mansi, et al. (1987) "Micro-Metasteses in Bone-Marrow in Patients with Primary Breast-Cancer-Evaluation as an Early Predictor of Bone Mestastases," *British Medical Journal*, 295:1093-1096.

Mansi, et al. (1999) "Outcome of primary-breast-cancer patients with micrometastases: a long-term follow-up study," *Lancet*, 354:197-202.

Meng et al., (2004) "Circulating tumor cells in patients with breast cancer dormancy," *Clinical Cancer Research* 10:8152-8162.

Messerschmidt (Sep. 2007) "Gradient Index Optical Microsystems Visualize Living Cells in Deep Tissue," *Grintech GmbH. Biophotonics International*, pp. 36-38.

Miao, Qin, et al., (2009) "Dual Modal three-dimensional Imaging of Single Cells using Optical Projection Tomography Microscope," *Journal of Biomedical Optics*, 14:3 pages.

Minkel, (Jul. 29, 2008) "Lensless On-Chip Microscope Inspired by "Floaters" in the Eye," *Scientific American*, 3 pp.

Moon, SanJun, et al., (Jul. 15, 2009) "Integrating Microfluidics and Lensless Imaging for point-of-care testing," *Biosensors and Bioelectronics*, 24(11):3208-3214.

Nott, Prabhu R., et al., (1994) "Pressure-driven flow of suspensions: simulation and theory,", *J. Fluid Mech.*, 275:157-199.

Nozokido, Tatsuo, et al., (2001) "Scanning Near-Field Millimeter-Wave Microscopy Using a Metal Slit as a Scanning Probe," *IEEE Transactions on Microwave Theory and Techniques*, 49(3):491-99.

Park, Sung Cheol, et al., (2003) "Super-resolution image reconstruction: a technical overview," *IEEE Signal Processing Magazine*, pp. 21-36.

Pastrana, Erika (Dec. 2011) *Nature Methods*, 8(12):999, 1 page [doi:10.1038/nmeth.1786].

Perkins et al., (1986) "Mutant Sensory Cilia in the Nematode *Caenorhabditis elegans,"* *Developmental Biology*, 117:456-487.

Popescu, G., et al., (Nov. 24, 2006) "Optical measurement of cell membrane tension," *Physical Review Letters* 97:218101-1-4.

Probstein, R. F., (2003) "Solutions of Uncharged Macromolecules and Particles," Chapter 5: pp. 109-116, p. 123; "Solutions of Electrolytes," Chapter 6: 190-197; "Surface Tension," Chapter 10: pp. 309-310; *Physicochemical Hydrodynamics*, Wiley, 2nd Edition.

Psaltis, Demetri, et al., (Jul. 2006) "Developing optofluidic technology through the fusion of microfluidics and optics," *Nature*, 442:381-386.

Resolution- "Airy Patterns and Resolution Criteria (3-D Version)," Olympus Fluo View Resource Center- Interactive Java Tutorials, [downloaded from the Internet on Jun. 12, 2013 at http://www.olympusconfocal.com/java/resolution3d], 3pp.

Ririe et al., (Dec. 23, 2008) "The *Caenorhabditis elegans* vulva: A post-embryonic gene regulatory network controlling organogenesis," *Proceedings of the National Academy of Sciences of the United States of America*, 105(51):20095-20099.

Rust, M. J., et al., (2006) "Sub-diffraction-limit imaging by stochastic optical reconstruction microscopy (STORM)," *Nature Methods*, 3:793-795.

Sarunic, et al., "PARS-OCT Endoscopy System," *Thorlabs*, downloaded on Aug. 5, 2013 from http://www.thorlabs.com/laserimaging/index.cfm?pageref=31&page=OCT-endoscopy, 2 pp.

Schultz, R., et al., (1998) "Subpixel Motion Estimation for Super-Resolution Image Sequence Enhancement," *Journal of Visual Communication and Image Representation*, 9(1):38-50.

Segre, G., et al., (1962) "Behavior of macroscopic rigid spheres in Poiseuille flow: Part 1. Determination of local concentration by statistical analysis of particle passages through crossed light beams," *J. Fluid Mech.*, 14:115-135.

Segre, G., et al., (1962) "Behavior of macroscopic rigid spheres in Poiseuille flow: Part 2. EXperimental results and interpretation," *J. Fluid Mech.*, 14:136-157.

Seo, Jeonggi, et al., "Disposable integrated microfluidics with Self-aligned planar microlenses," *Sensors and Acutators B*, vol. 99, pp. 615-622 (2004).

Shi, J., et al., (2006) "Small-kernel superresolution methods for microscanning imaging systems," *Applied Optics*, 45(6):1203-1214.

Stanley, S.L., "Amoebiasis," *Lancet* 361, pp. 1025-1034 (2003).

(56) References Cited

OTHER PUBLICATIONS

Stone, H.A., et al., (2004) "Engineering Flows in Small Devices: Microfluidics Toward a Lab-on-a-Chip," *Annu. Rev. Fluid Mech.*, 36:381-411.

Su, Ting-Wei, et al., (Apr. 26, 2010) "Multi-angle lensless digital holography for depth resolved imaging on a chip," *Optics Express*, OSA, Washington DC, US 18(9):1094-4087, 22pp.

Svitil, (Jul. 28, 2008) "Microscope on a Chip," *Caltech Bioengineers Develop, Caltech Media Relations*, downloaded from http://www.caltech.edu/content/caltech-bioengineers-develop-microscope-chip, 2pp.

Tai, Y. C., et al., (2002) "Integrated micro/nano fluidics for mass-spectrometry protein analysis," *International Journal of Nonlinear Sciences and Numerical Simulation*, 3(3-4):739-741.

Tearney, G. J., et al., (1996) "Scanning single-mode fiber optic catheter-endoscope for optical coherence tomography," *Optics Letters*, 21:543-545.

Thorsen, Todd, et al., (2002) "Microfluidic Large-Scale Integration," *Science*, 298:580-584.

Tindol, (Sep. 5, 2006) "Caltech Researchers Announce Invention of the Optofluidic Microscope," *Caltech Media Relations*, 2 pp.

Walker, Glenn, and Beebe, David, (2002) "A Passive Pumping Method for Microfluidic Devices," *Lab on Chip*, pp. 131-134.

Wiedswang et al., (2004) "Isolated Tumor Cells in Bone Marrow Three Years after Diagnosis in Disease-Free Breast Cancer Patients Predict Unfavorable Clinical Outsome," *Clinical Cancer Research*, 10:5342-5348.

Woelfle et al., (2005) "Bi-specific immunomagnetic enrichment of micrometastatic tumour cell clusters from bone marrow of cancer patients," *Journal of Immunological Methods* 300:136-145.

Woelfle et al., (2005) "Influence of immunomagnetic enrichment on gene expression of mor cells," *Journal of Translational Medicine* 3:12, 6 pp.

Woo (Spring 2009) "A Toymaker's Lab," *Engineering & Science*, pp. 22-27.

Wu, J., Cui, X., Lee, L. M., and Yang, C., (2008) "The application of Fresnel zone plate based projection in optofluidic microscopy," *Opt. Exp.* 16(20):15595-15602.

Yang, et al. (Jul. 2006) "Optofluidics can create small, sheap biophotonic devices," *Laser Focus World*, 42(6):85-8c.

Yang, et al. (Dec. 2006) "Optofluidics Reinvents the Microscope," *Laser Focus World*, 42(12):83-86.

Yang et al. (Spring 2007) "Building a Microscopic Microscope," *ENGenious—Progress Report*, Spring 2007, pp. 44-47.

Yang et al. (2008) "New Micro-Microscope is Portable and Cheap," *National Public Radio, Interview: Talk of the Nation*, 11 pp.

Yang et al. "Optofluidics: Optofluidics Enhances Cytometry," *BioOptics World*, downloaded on Aug. 5, 2013 from http://bioopticsworld.com/articles/print/volume-2/issued-1/fe atures/feature-focus/optofl . . . , 6pp.

Yanowitz, et al., (2005) "Cyclin D involvement demarcates a late transition in *C. elegans* embryogenesis," *Developmental Biology*, 279:244-251.

Zheng, et al., (2010) "Sub-pixel resolving optofluidic microscope for on-chip cell imaging," *Lab on a Chip*, 10(2):3125-3129.

Zheng, et al., (2009) "Supplementary Information for: Sub-pixel resolving optofluidic microscope for on-chip cell imaging," *Supplementary Material (ESI) for Lap on a Chip*, 10:3 pages.

Zheng, et al., (Oct. 15, 2011) "Microscopy refocusing and dark-field imaging by using a simple LED array," *Optics Letters* 36(20):3987-3989.

Zheng et al., (2011) "The ePetri dish, an on-chip cell imaging platform based on subpixel perspective sweeping microscopy (SPSM)," 6 pages and "Supporting Information" 3 pages; *Proceedings of the National Academy of Science* 108(41):16889-94.

Zhu, et al., (2004) "Filter-based microfluidic device as a platform for immunofluorescent assay of microbial cells," *Lab Chip*, 4:337-341; published as Advanced Article on Apr. 5, 2004 at http://pubs.rsc.org |DOI: 10.1039/b401834f.

United States Patent and Trademark Office (USPTO) Office Action in U.S. Appl. No. 13/281,287 dated on Nov. 6, 2014.
United States Patent and Trademark Office (USPTO) Office Action in U.S. Appl. No. 13/411,302 dated on Jan. 5, 2015.
United States Patent and Trademark Office (USPTO) Office Action in U.S. Appl. No. 14/072,652 dated on Mar. 23, 2015.
United States Patent and Trademark Office (USPTO) Final Office Action in U.S. Appl. No. 13/411,103 dated on Oct. 2, 2014.
Chinese Second Office Action dated Oct. 8, 2014 issued in CN 201180012251.6.
Chinese First Office Action [no translation] dated Jan. 20, 2015 issued in CN 201180048639.1.
Japanese Office Action [with translation] dated Oct. 28, 2014 issued in JP 2013536747.
Chinese First Office Action dated Feb. 28, 2015 issued in CN201280003668.
"Fresnel number," Wikipedia, last modified May 2, 2010, 2pp.
"Zone plate," Wikipedia, last modified Apr. 2, 2009.
Aigouy, L., et al., (2007) "Near-field analysis of surface waves launched at nanoslit apertures," *Physical Review Letters*, 98:153902.
Balic et al., (Oct. 1, 2006) Human Cancer Biology: "Most Early Disseminated Cancer Cells Detected in Bone Marrow of Breast Cancer Patients Have a Putative Breast Cancer Stem Cell Phenotype," *Clinical Cancer Res.* 12(19):5615-5621 [Downloaded from clincancerres.aacrjournals.org on May 21, 2015].
Cui, Xiquan, et al., (Jan. 2006) "Portable optical microscope-on-a-chip," *Proc. SPIE*, 6095:609509-1-609509-8.
Dunn, et al., (2007) "Introduction to Confocal Microscopy," [retrieved on Aug. 2, 2007 at available at http://www.microscopyu.com/articles/confocal], *MicroscopyU*, 3 pp.
Levin-Reisman, I., et al., (2010) "Automated imaging with ScanLag reveals previously undetectable bacterial growth phenotypes," *Nat Meth*, 7(9):737-739.
Tai, Y. C., et al., (2002) "Integrated micro/nano fluidics for mass-spectrometry protein analysis," *International Journal of Nonlinear Sciences and Numerical Simulation*, 3(34):739-741.
Wang et al., (2009) "Characterization of acceptance angles of small circular apertures," *Optics Express* 17(26):23903-23913.
Wu, J., et al., (Jul. 1, 2010) "Wide field-of-view microscope based on holographic focus grid illumination," *Optics Letters*, 35(13):2188-2190.
Zheng et al., (Jul. 28, 2013) "Wide-field, high-resolution Fourier ptychographic microscopy," *Nature Photonics | Advance Online Publication*, DOI 10.1038/NPHOTON.2013.187, 19 pages.
United States Patent and Trademark Office (USPTO) Final Office Action in U.S. Appl. No. 13/281,287 dated on Jul. 1, 2015.
United States Patent and Trademark Office (USPTO) Final Office Action in U.S. Appl. No. 13/411,302 dated on Sep. 25, 2015.
United States Patent and Trademark Office (USPTO) Final Office Action in U.S. Appl. No. 14/072,652 dated on Nov. 6, 2015.
United States Patent and Trademark Office (USPTO) Office Action in U.S. Appl. No. 13/411,103 dated on Jun. 17, 2015.
United States Patent and Trademark Office (USPTO) Notice of Allowance in U.S. Appl. No. 13/411,103 dated on Jan. 4, 2016.
Chinese Third Office Action dated Apr. 27, 2015 issued in CN 201180012251.6.
European Examination Report dated Jun. 5, 2015 issued in EP 11 760 112.0.
European Office Action dated Jun. 5, 2015 issued in EP 11 836 959.4.
Japanese Office Action [with translation] dated Jun. 23, 2015 issued in JP 2013536747.
European Examination Report dated Jun. 5, 2015 issued in EP 12 75 2493.
Japanese Office Action dated Oct. 6, 2015 issued in JP 2013-556657.
Biener, G., et al., (2011)"Combined reflection and transmission microscope for telemedicine applications infield settings," *Lab Chip*, 11(16):2738-2743.
Borenfreund, E. & Puerner, J. A., (1985) "Toxicity determined in vitro by morphological alterations and neutral red absorption," *Toxicology Letters* 24:119-124.

(56) References Cited

OTHER PUBLICATIONS

Breslauer, D., et al., (Jul. 2009) "Mobile Phone Based Clinical Microscopy for Global Health Applications" *PLoS One*, 4(7):e6320, 7pp.
Cavanaugh, P.F. et al., (1990) "A semi-automated neutral red based chemosensitivity assay for drug screening," *Investigational new drugs* 8:347-354.
Cohen, A.R., Gomes, F. L.A.F., Roysam, B.& Cayouette, M., (Mar. 2010) "Computational prediction of neural progenitor cell fates," *Nature Methods*, 7(3):213, 10pp.
Costa, M. R. et al., (2011) "Continuous live imaging of adult neural stem cell division and lineage progression in vitro," *Development* 138(6):1057-1068.
Crane, M., Chung, K., Stirman, J. & Lu, H., (2010) "Microfluidics-enabled phenotyping, imaging, and screening of multicellular organisms," *Lab on a Chip* 10:1509-1517.
Denis, L., Lorenz, D., Thiebaut, E., Fournier, C., Trede, D., (2009) "Inline hologram reconstruction with sparsity constraints," *Opt Lett*, 34:3475-3477.
Dykstra, B. et al., (May 23, 2006) "High-resolution video monitoring of hematopoietic stem cells cultured in single-cell arrays identifies new features of self-renewal," *PNAS*, 103(21):8185-8190.
Eilken, H.M., Nishikawa, S.I. & Schroeder, T. (Feb. 2009) "Continuous single-cell imaging of blood generation from haemogenic endothelium," *Nature* 457:896-900.
Farsiu S. et al., (Jan. 2006) "Multiframe Demosaicing and Super-Resolution of Color Images," *IEEE Transactions on Image Processing*, 15(1): 141-159.
Farsiu, S., Robinson, D., Elad, M. & Milanfar, P., (2004) "Advances and Challenges in Super Resolution," *International Journal of Imaging Systems and Technology* 14:47-57.
Fienup, J.R., (Jul. 1978)"Reconstruction of an object from the modulus of its Fourier transform," *Opt Lett*, 3(1):27-29.
Garcia-Sucerquia, J., et al., (Feb. 2006) "Digital in-line holographic microscopy," *Appl. Opt.*, 45(5): 836-850.
Hardie, R., Barnard, K., and Armsrong, E.E., (Dec. 1997) "Joint MAP Registration and High-Resolution Image Estimation Using a Sequence of Undersampled Images," *IEEE Transactions on Image Processing* 6(12):1621-1633.
Hou, H., et al., (2010) "Deformability based cell margination—A simple microfluidic design for malaria infected erythrocyte separation," *Lab on a Chip* 10:2605-2613.
Isikman, S.O., et al., (May 3, 2011) "Lens-free optical tomographic microscope with a large imaging volume on a chip," *PNAS USA*, 108(18):7296-7301.
Koren, G., Polack, F., Joyeux, D., (Mar. 1993) Iterative algorithms for twin-image elimination in in-line holography using finite-support constraints, *J Opt Soc Am A* 10:423-433.
Lai, S., King, B., Neifeld, M.A., (2000) "Wave front reconstruction by means of phase-shifting digital in-line holography," *Opt Commun.*, 173:155-160.
Li, W., Knoll, T., Thielecke, H., (2010) "On-chip integrated lensless microscopy module for optical monitoring of adherent growing mammalian cells," *Engineering in Medicine and Biology Society (EMBC), 2010 32nd Annual International Conference of the IEEE*, pp. 1012-1015.
Liu, G. and Scott, P., (Jan. 1987) "Phase retrieval and twin-image elimination for in-line Fresnel holograms," *J Opt Soc Am A*, 4(1):159-165.
Malek M., Aliano, D., Coëtmellec, S., Lebrun, D., (May 17, 2004) "Digital in-line holography: Influence of the shadow density on particle field extraction," *Opt. Express*, 12(10):2270-2279.
Medoro, G. et al. (2003) "A Lab-on-a-Chip for Cell Detection and Illumination," *IEEE Sensors Journal*, 3(3): 317-325.
Miao, Q., Rahn, J.R., Tourovskaia, A., Meyer, M.G., Neumann, T., Nelson, A.C., and Seibel, E.J., (Dec. 21, 2009) "Dual-modal three dimensional imaging of single cells with isometric high resolution using an optical projection tomography microscope," *J. Biomed. Opt.* 14(6):064034, 6pp.
Micó, V., Garcia, J., Zalevsky, Z., and Javidi, B., (Oct. 2010) "Phase-Shifting Gabor Holographic Microscopy," *J Disp Technol*, 6(10):484-489.
Milanfar, P., (2010) "Super-Resolution Imaging," *CRC Press*, 9pp.
Mudanyali, O., et al., (Jun. 7, 2010) "Compact, light-weight and cost-effective Microscope based on Lensless Incoherent Holography for Telemedicine Applications," *Lab on a Chip*, 10:1417-1428, 25 pp.
Repetto, G., Del Peso, A. & Zurita, J.L., (2008) "Neutral red uptake assay for the estimation of cell viability/cytotoxicity," *Nature Protocols* 3(7):1125-1131.
Rodenburg, J.M., Hurst, A.C., Cullis, A.G., (2007) "Transmission microscopy without lenses for objects of unlimited size, " *Ultramicroscopy*, 107:227-231.
Schroeder, T., (2011) "Long-term single-cell imaging of mammalian stem cells," *Nature Methods Supplement* 8(4):S30-S35.
Schultz, R.R., Meng, L., Stevenson, R.L., (1998) "Subpixel motion estimation for superresolution image sequence enhancement," *Journal of Visual Communication and Image Representation*, 9(1):38-50.
Seo, et al., (2009) "Lensfree holographic imaging for on-chip cytometry and diagnostics," *Lab on a Chip*, 9(6):777-787.
Xu, et al. (2001) "Digital in-line holography for biological applications," *PNAS USA*, 98:11301-11305.
Xu, L., Miao, J., Asundi, A., (Dec. 2000) "Properties of digital holography based on in-line configuration, " *Opt Eng*, 39(12):3214-3219.
Zhang, F., Pedrini, G., and Osten, W., (2007) "Phase retrieval of arbitrary complex-valued fields through apertureplane modulation," *Phys Rev A*, 75:043805, 4pp.
United States Patent and Trademark Office (USPTO) Notice of Allowance in U.S. Appl. No. 13/281,287 dated on May 25, 2016.
European Examination Report dated Feb. 2, 2016 issued in EP 12 75 2493.
U.S. Notice of Allowance in U.S. Appl. No. 13/411,302 dated Oct. 25, 2016.
U.S. Notice of Allowance in U.S. Appl. No. 14/072,652 dated Oct. 24, 2016.
Chinese Office Action [no translation] dated Nov. 3, 2014 issued in CN 201280011370.4.
U.S. Notice of Allowance in U.S. Appl. No. 13/411,302 dated Feb. 2, 2017.
U.S. Notice of Allowance in U.S. Appl. No. 14/072,652 dated Jan. 12, 2017.

\* cited by examiner

SUPER RESOLUTION OPTOFLUIDIC MICROSCOPES FOR 2D AND 3D IMAGING

CROSS-REFERENCES TO RELATED APPLICATIONS

This is a non-provisional application of, and claims priority to, U.S. Provisional Patent Application No. 61/316,762 entitled "Super Resolution Optofluidic Microscope for 2D and 3D Imaging" filed on Mar. 23, 2010. That provisional application is hereby incorporated by reference in its entirety for all purposes.

This non-provisional application is related to the following co-pending and commonly-assigned patent application, which is hereby incorporated by reference in its entirety for all purposes:

U.S. patent application Ser. No. 12/398,050 entitled "Optofluidic Microscope Device with Photosensor Array" filed on Mar. 4, 2009.

BACKGROUND OF THE INVENTION

Embodiments of the present invention generally relate to optofluidic microscopes devices (OFMs) and OFM systems. More specifically, certain embodiments relate to super resolution optofluidic microscope (SROFMs) for subpixel resolution, two-dimensional and three-dimensional imaging.

The miniaturization of biomedical imaging tools has the potential to vastly change methods of medical diagnoses and scientific research. More specifically, compact, low-cost microscopes could significantly extend affordable healthcare diagnostics and provide a means for examining and automatically characterizing a large number of cells, as discussed in Psaltis, D., et al., "*Developing optofluidic technology through the fusion of microfluidics and optics,*" Nature, Vol. 442, pp. 27, s.1. (2006), which is hereby incorporated by reference in its entirety for all purposes.

Conventional optical microscopes have bulky optics, and have proven to be expensive and difficult to miniaturize. Recent developments in microfluidic technology offer optofluidic microscopes (OFMs) which have been proven to be low cost, compact devices with the high throughput provided by microfluidics. An example of a conventional OFM can be found in Cui, Xiquan, et al., "*Lensless high-resolution on-chip optofluidic microscopes for Caenorhabditis elegans and cell imaging,*" Proceedings of the National Academy of Science, Vol. 105, p. 10670 (2008), which is hereby incorporated by reference in its entirety for all purposes. However, conventional OFMs rely on an aperture array or a photosensor array diagonally extending across the fluid channel to acquire images as object(s) move across the array. Thus, acquisition time in conventional OFMs depends on how long it takes the object to move across the array. Also, image resolution in many conventional OFMs was limited.

BRIEF SUMMARY OF THE INVENTION

Embodiments of the present invention relate to SROFMs for super resolution (e.g., subpixel resolution), two-dimensional and three-dimensional imaging. A SROFM includes a fluid channel and a two-dimensional light detector. The light detector samples data at a subpixel sampling rate to capture a sequence of subpixel shifted frames of projection images as an object being imaged moves through the fluid channel. A super resolution two-dimensional image can be generated using a super-resolution algorithm with the sequence of subpixel shifted frames and a motion vector of the object. A super resolution three-dimensional image can be computed with a tomography algorithm from a plurality of sequences (multiple sequences) of subpixel shifted frames based on different angles of incident light.

One embodiment is directed to a SROFM having a body defining a fluid channel having a longitudinal axis. The body includes a surface layer proximal the fluid channel. The surface layer has a two-dimensional light detector array configured to receive light passing through the fluid channel and sample a sequence of subpixel shifted projection frames as an object moves through the fluid channel. The SROFM also has a processor in electronic communication with the two-dimensional light detector array. The processor is configured to generate a high resolution image of the object using a super resolution algorithm and based on the sequence of subpixel shifted projection frames and a motion vector of the object.

Another embodiment is directed to a SROFM comprising a body defining a fluid channel having a longitudinal axis. The body includes a surface layer proximal the fluid channel. The SROFM further comprises a two-dimensional light detector array in the surface layer. The two-dimensional light detector array is configured to receive light of different wavelengths as an object through the fluid channel and configured to sample a plurality of sequences of subpixel shifted projection frames associated with different wavelengths. In some cases, the SROFM also comprises a processor in electronic communication with the two-dimensional light detector array. The processor is configured to generate a plurality of high resolution images associated with the different wavelengths using a super resolution algorithm and based on the plurality of sequences of subpixel shifted projection frames and a motion vector. In one of these cases, the processor is also configured to combine the plurality of high resolution images based on different wavelengths to form a color high resolution image of the object. In this case, the processor is further configured to use an image recognition algorithm to diagnose conditions or disease based on the color high resolution image of the object.

Another embodiment is directed to a SROFM comprising a body defining a fluid channel having a longitudinal axis. The body includes a surface layer proximal the fluid channel. The SROFM further comprises a two-dimensional light detector array in the surface layer. The two-dimensional light detector array is configured to receive light of different incidence angles as an object through the fluid channel and is configured to sample a plurality of sequences of subpixel shifted projection frames associated with different incidence angles.

Another embodiment is directed to a mobile SROFM comprising a body defining a fluid channel having a longitudinal axis. The body includes a surface layer proximal to the fluid channel. The surface layer has a light detector configured to receive light passing through the fluid channel and sample a sequence of subpixel shifted projection frames as an object moves through the fluid channel. The SROFM further comprises a mobile communication device (e.g., smartphone) having a processor and a display. The processor is in electronic communication with the light detector. The processor is configured to generate a high resolution image of the object using a super resolution algorithm and based on the sequence of subpixel shifted projection frames and a motion vector. The processor is further configured to display the high resolution image on the display of the mobile communication device.

Another embodiment is directed to a method of generating a high resolution image of an object using a super resolution optofluidic microscope device having a body defining a fluid channel and including a surface layer proximal to the fluid channel, the surface layer having a two-dimensional light detector array. The method comprises illuminating the fluid channel. The method further comprises sampling, by the two-dimensional light detector array, a sequence of subpixel shifted projection frames as an object moves through the fluid channel. The method further comprises reconstructing, by a processor, the high resolution image using a super resolution algorithm based on the sequence of subpixel shifted projection frames and a motion vector.

Another embodiment is directed to a method of generating a three-dimensional high resolution image of an object using a super resolution optofluidic microscope device having a body defining a fluid channel and including a surface layer proximal to the fluid channel, the surface layer having a two-dimensional light detector array. The method comprises illuminating the fluid channel with light of different incidence angles at different sampling times. The method further comprises sampling, by the two-dimensional light detector array, a plurality of sequences of subpixel shifted projection frames as an object moves through the fluid channel, each sequence associated with a different incidence angle. The method further comprises reconstructing, by a processor, a plurality of high resolution images associated with different incidence angles using a super resolution algorithm and based on the plurality of sequences of subpixel shifted projection frames and a motion vector. The method further comprises computing, by the processor, the three-dimensional high resolution image using a tomography algorithm and based on the plurality of super-resolution images associated with different incident angles.

These and other embodiments of the invention are described in further detail below.

DETAILED DESCRIPTION OF THE INVENTION

Figure 1:
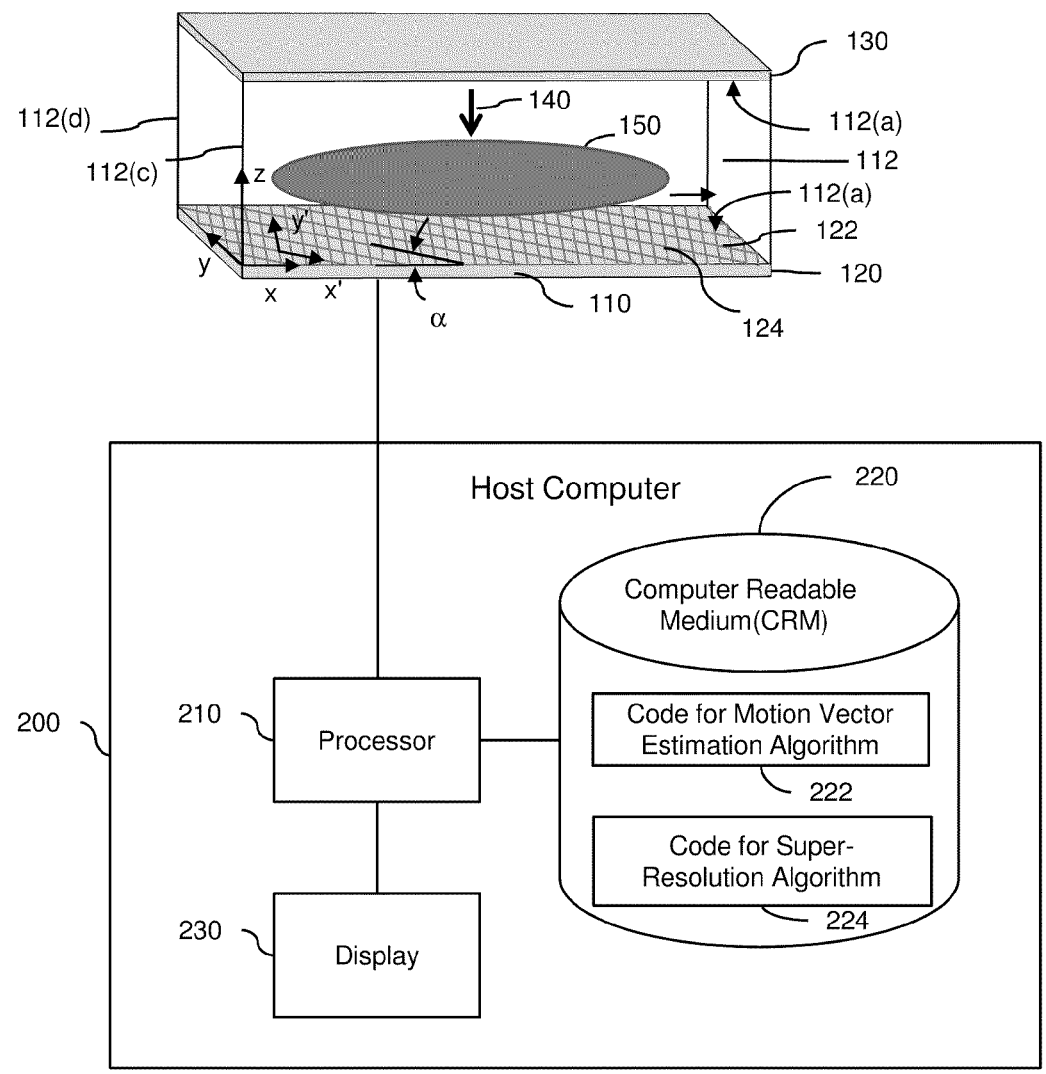
FIG. 1 is a schematic diagram of components and partial components of a SROFM, according to embodiments of the invention.

Embodiments of the present invention will be described below with reference to the accompanying drawings. Some embodiments include a SROFM have a body (e.g., microfluidic chip) defining a fluid channel and a light detector with a two-dimensional array of light detecting elements (e.g., CMOS sensor array). The light detector samples light data at a subpixel sampling rate to capture a sequence of subpixel-shifted snapshot projections (frames) as the object moves through the fluid channel. The processor determines the motion vector of the object. Then, the processor uses a super resolution algorithm (SR algorithm) to reconstruct a super-resolution (SR) two-dimensional image of an object from the sequence of subpixel-shifted frames and the motion vector. The processor can also determine a SR, three-dimensional image of the object by combining multiple reconstructed HR images from different incidence angles (views) using computed tomography.

The subpixel shifts of the object between frames is semi-controlled by the microfluidic flow within the confines of the fluid channel and/or any techniques used to control fluid flow or particulate transport. This semi-controlled subpixel movement between frames allows for a more accurate motion vector estimation and reconstruction of HR images of a microscopic objects without the need of bulky controllers and actuators.

Embodiments of the invention provide one or more technical advantages. A general advantage is that the SROFM uses a high sampling rate in the time domain (e.g., subpixel sampling rate) to offset the sub-Nyquist rate sampling in the spatial domain of the projection images, combining work done in super resolution imaging with optofluidic microscopy to provide a simple, low cost, high throughput microscopy device with significant resolution enhancement. A more specific advantage is that the SROFM of embodiments can be easily miniaturized. The SROFM can be easily miniaturized since it does not require bulky optics, motion controller or actuator needed in other microscanning schemes, or an on-board illumination source. Also, most of the SROFM can be in the form of a microfluidic chip. A miniaturized SROFM can provide a compact, inexpensive, and portable imaging system that may fulfill many needs in biological research, point-of-care analysis and field diagnostics. A miniaturized SROFM could also bring affordable healthcare diagnostics to less developed populations in rural settings, where it is too costly to deploy expensive conventional microscopes and skilled technicians. Another advantage is the elimination of the aperture array from the conventional OFM design. The SROFM eliminates the need of having an aperture array, which can simplify fabrication of the SROMFM and thus, reduce cost. Another advantage is that the SROFM has microfluidic flow of a fluid specimen across the light detector which allows for manipulation of the objects being imaged in subpixel shifts, and eliminates the need for a precision scanning setup needed in other super resolution devices. Another advantage is that the SROFM takes snapshot frames with a two-dimensional array over subpixel shifts. Many frames can be acquired over a short distance so that an HR image can be acquired without having the object pass over the entire array. Thus, acquisition time is reduced, which can improve throughput rates. Reducing acquisition time may also reduce exposure of the object being imaged to light, which can reduce the risk of damaging the object. Other advantages are provided in Section IIB.

I. SROFM

FIG. 1 is a schematic diagram of components and partial components of a SROFM 10, according to embodiments of the invention. The SROFM 10 includes a body 110 which defines or includes a fluid channel 112. Portions of the body 110 may be in the form of a microfluidic chip in many embodiments. In FIG. 1, the body 110 including a straight portion of the fluid channel 112. The fluid channel 112 includes a first surface 112(a) and a second surface 112(b) on opposite sides of the fluid channel 112. The first surface 112(a) corresponds to an inner surface which may be at the bottom/top of the fluid channel 112. The second surface 112(b) corresponds to an inner surface at the opposite side of the fluid channel 112 from the first surface 112(a). The fluid channel 112 also includes two opposing lateral surfaces, a first lateral surface 112(c) and a second lateral surface 112(d). In addition, the body 110 includes a first surface layer 120 and an opposing second surface layer 130. The first surface layer 120 includes a light detector 122 in the form of a two-dimensional array of light detecting elements 124 (two-dimensional light detector array). In FIG. 1, an object 150 being imaged is shown moving through the fluid channel 112 illuminated by incident light 140 from an illumination source (not shown). In operation, the SROFM 10 directly images the object 150 onto the light detector 122.

The SROFM 10 also includes a host computer 200 (e.g., smartphone) having a processor 210, a computer readable medium (CRM) 220 in electronic communication with the processor 210, and a display 230 in electronic communication with the processor 210. The CRM 220 includes code with a motion estimation algorithm 222 and code with a SR algorithm 224. The CRM 220 may include other code (e.g., code with a tomography algorithm) in other embodiments.

The SROFM 10 also includes an x-axis, a y-axis, and a z-axis. The x-axis lies along a longitudinal axis of the fluid channel 112. The x-axis and y-axis lie in the plane of the inner surface of the first surface layer 120. The z-axis is orthogonal to this plane.

In many illustrated examples such as the one shown in FIG. 1, the SROFM 10 includes a multi-layer body 110 that includes or defines a fluid channel 112. In many embodiments, the multi-layer body 110 is a microfluidic chip. In FIG. 1, the multi-layer body 110 includes a first surface layer 120 that is an inner surface layer of the fluid channel 112. The inner surface of the first surface layer 120 is coincident with the first surface 112(a) of the fluid channel 112. The first surface layer 120 lies proximal the fluid channel 112. The light detector 122 is located on or within the first surface layer 120 of the multi-layer body 110. The body multi-layer 110 also includes a second surface layer 130 that is another inner surface layer of the fluid channel 112. The inner surface of the second surface layer 130 is coincident with the second surface 112(b) of the fluid channel 112. The second surface layer 130 also lies proximal the fluid channel 112. Although illustrated examples show the body 110 as a multi-layer structure, other embodiments may include a body 110 that is a monolithic structure.

The layers of the multi-layer body 110 of embodiments may be made of any suitable material (e.g., Polydimethylsiloxane (PDMS)) or combination of materials of any suitable thickness or thicknesses, and may include suitable device(s) (e.g., light detector 122). In one exemplary embodiment, the multi-layer body 110 consists of a micromolded Polydimethylsiloxane (PDMS) microfluidic chip bonded directly to a CMOS sensor. In some cases, the multi-layer body 110 may be fabricated using standard semiconductor and micro/nanofabrication procedures.

Although illustrated embodiments show certain layers in the multi-layer body 110, other embodiments may integrate, omit, or add one or more layers or change the location of one or more layers in the multi-layer body 110. For example, a multi-layer body 110 of an embodiment may include a transparent protective layer that covers the first surface layer 120 to isolate the light detecting elements 124 from the fluid and objects 150 moving through the fluid channel 112 of the SROFM 10.

In FIG. 1, the fluid channel 112 includes a first surface 112(a) and an opposing second surface 112(b). The fluid channel 112 also includes a first lateral surface 112(c) and an opposing second lateral surface 112(d). The fluid channel 112 also has a longitudinal axis along the x-axis. Although a single fluid channel 112 is shown in FIG. 1, other embodiments may include additional fluid channels 112 for parallel processing.

The dimensions of the fluid channel 112 may be of any suitable size. For example, the width and/or height of the fluid channel 112 may each be less than about 10 microns, 5 microns, or 1 micron.

In some embodiments, the dimensions (geometry) of the fluid channel 112 are sized to improve or maximize image quality. Due to the scattering angle of light 140 passing through the object 150 being imaged, projection image quality can be degraded if the object 150 being imaged is flowed away from the first surface 112(a) of the light detector 122. For this reason, the quality of images can be better for objects 150 with smaller thicknesses, especially for the size range of eukaryotic cells. In these embodiments, the channel height may be sized based on the size of the objects 150 being imaged by the SROFM 10 to flow the objects 150 close to the first surface 112(a). Hence, the channel height is sized to be just slightly larger than the size of the objects 150 being imaged. For example, the channel height may be 10 micron where objects 150 being imaged are 8 micron in order to keep the objects 150 close to the first surface layer 120, which may help improve the quality of the images generated by the SROFM 10.

Figure 2:
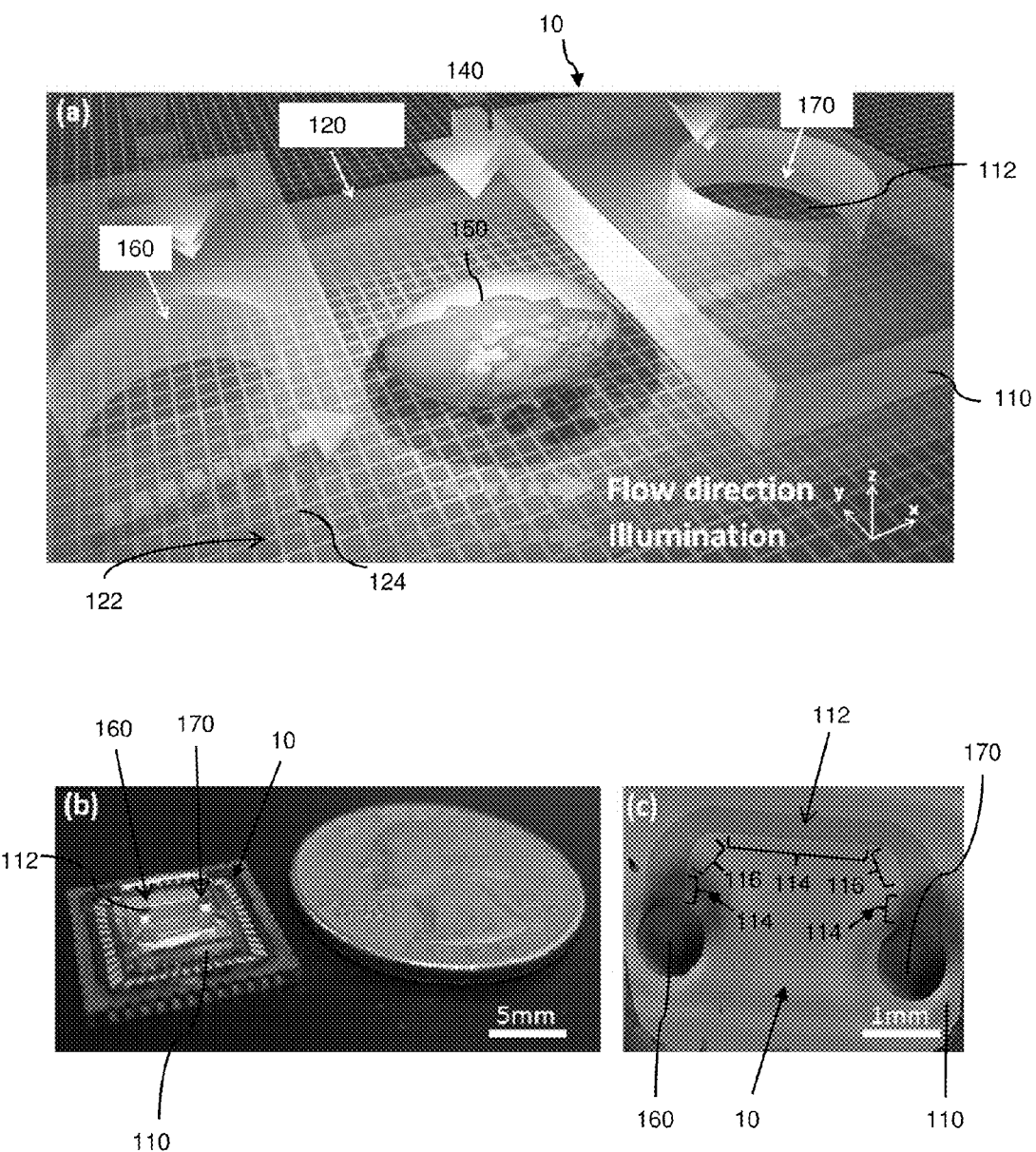
FIG. 2(a) is a schematic drawing of components of a SROFM comprising a micromolded PDMS microfluidic chip bonded directly to a complementary metal-oxide-semiconductor (CMOS) sensor, according to embodiments of the invention.
FIG. 2(b) is a photograph of the body of a SROFM in the form of a microfluidic chip next to a quarter for scale, according to embodiments of the invention.
FIG. 2(c) is an image of a portion of the SROFM of FIG. 2(a), according to embodiments of the invention.

The fluid channel 112 can have any suitable shape (e.g., linear, U-shaped, S-shaped, substantially circular shaped, etc.). In non-linear shaped fluid channels 112, the fluid channel 112 can be comprised of a series of straight portions 114 and/or curved portions 116 (shown in FIG. 2(c)). For example, the fluid channel 112 may be U-shaped with two curved portions 116 in the corners and three straight portions 114 at the edges and in between curved portions 116. An illustrated example of a U-shaped fluid channel 112 is shown in FIG. 2(c). FIG. 1 is an illustrated example of a straight portion 114 of the U-shaped fluid channel 112 shown in FIG. 2(c).

In embodiments, the fluid channel 112 can include a fluid flow that carries a fluid specimen with one or more objects 150 being imaged through the fluid channel 112 in the general direction of the longitudinal axis of the fluid channel 112. Any suitable technique of controlling fluid flow and/or particulate transport can be used to move the object(s) 150 through the fluid channel 112. Some convention techniques include pressure drive flow, electrokinetic transport, discrete droplet translocation via electrowetting, or thermocapilarity techniques. Other techniques may include gravity drive flow, hydrodynamic focusing, dielectrophoresis, and optical tweezing. Any suitable control device(s) may be used to control the flow of fluid and/or movement of the object 150 through the fluid channel 112. Some examples of suitable control devices include micropumps, direct current (DC) electrokinetic devices, dielectrophoresis electrodes, and/or hydrodynamic focusing channels.

The fluid channel 112 also includes an inlet 160 and an outlet 170 connected to portions, typically opposite ends, of the fluid channel 112. An inlet 160 can refer to a port where the fluid specimen can be introduced into the fluid channel 112. An outlet 490 can refer to a port where the fluid specimen with the object(s) being imaged can exit the fluid channel 112. An illustrated example of an inlet 160 and outlet 170 can be found in FIG. 2.

One or more illumination sources provide incident light 140 to the fluid channel 112. The illumination source(s) may be a component of the SROFM 10 or may be separate from the SROFM 10. In many embodiments, the SROFM 10 does not require specific illumination sources, making it a suitable solution for low-cost, portable microscopy. The illumination source(s) may be any suitable device or other source of light such as ambient light. Suitable illumination sources are naturally and commercially available. For example, a SROFM 10 with a light detector 122 having an exposure time of 0.3 ms can use an illumination source of typical room light (300~500 lux). Even shorter exposure times can be used for imaging under the illumination source of sunlight (~10000 lux). In another example, the illumination source may be a conventional LED lamp (about 2 Watt) with a light intensity comparable to ambient room light on the order of 80 lumens. Because the quality of image does not depend on the type of illumination used in many embodiments, the SROFM 10 may be implemented in low-cost, cell-phone-based (e.g., smartphone-based) or USB-based portable miniature microscopes, since there is no need for a particular scanning or coherent illumination scheme or on-board illumination source.

The illumination source(s) may provide light 140 of any suitable wavelength(s), intensity(ies), polarization(s), phase(s), and/or incidence angle(s). In one embodiment, the illumination source(s) can provide light 140 of n different wavelengths $\lambda_1, \ldots, \lambda_n$ at different times during sampling. Any suitable number of wavelengths may be used (e.g., n=1, 2, 3, 4, 5, . . . , 20). For example, an illumination source(s) may provide RGB illumination of three wavelengths $\lambda_1, \lambda_2,$ and $\lambda_3$ corresponding to red, green, blue colors. Also, the illumination source(s) may be placed in any suitable location to provide incident light 140 that which can pass through the object 150 and that provides n desired incidence angles, $\theta_1, \ldots \theta_n$, where n=1, 2, 3, 4, 5, etc.

Any suitable object 150, portion of an object 150, or number of objects 150 may be imaged by the SROFM 10. Suitable objects 150 can be biological or inorganic entities. Examples of biological entities include whole cells, cell components, microorganisms such as bacteria or viruses, cell components such as proteins, etc. Inorganic entities may also be imaged by embodiments of the invention.

The SROFM 10 also includes a light detector 122 (e.g., photosensor) having a local x' axis and y' axis at the plane of the first surface 112(a). A light detector 122 refers to any suitable device capable of generating one or more signals with light data based on light received by the light detector 122. The signals with light data may be in the form of an electrical current from the photoelectric effect. The light detector 122 includes discrete light detecting elements 124 (pixels) in the form of a two-dimensional array of light detecting elements 124 (shown in FIG. 1). The light detecting elements 124 are located on or within the first surface layer 120 of the body 110.

In some embodiments, the two-dimensional array of light detecting elements 124 is oriented at an angle α (shown in FIG. 1) with respect to the longitudinal axis of the fluid channel 112. By oriented the two-dimensional array at an angle, an object 150 moving with the fluid flow generally along the longitudinal axis of the fluid channel 112 also translates in both the x'-direction and y'-direction of the local axes of the two-dimensional array of light detecting elements 124. In these embodiments, the fluid channel 112 may have been placed, during fabrication, onto the light detector 122 at the angle α to orient the light detecting elements 124 in this way.

Any suitable angle α may be used. In some cases, the angle α used has been determined to allow the SROFM 10 to generate LR images at specific subpixel translations in both x' and y' directions that will be suitable for accurate motion vector estimation and HR image data reconstruction. In some cases, the angle α used has been determined to maximize the frame sampling rate by using fewer pixel rows in the two-dimensional array in the imaging area of interest. In one example, an angle α ranging from 10-30 degrees has been determined to provide sufficient displacement along the y-direction for HR image data reconstruction and also to maximize the frame sampling rate by using fewer pixel rows in the imaging area of interest. In one embodiment, the imaging area of inters is about 250 micron*2.5 mm.

Any suitable light detector 122 can be used. Some examples of suitable light detectors 122 having two-dimensional arrays of light detecting elements 124 include a charge coupled device (CCD) array, a CMOS array, an avalanche photo-diode (APD) array, a photo-diode (PD)

array, and a photomultiplier tubes (PMT) array. These light detectors 122 and others are commercially available.

Any suitable type of light detector 122 can be used. Some examples of suitable types of light detectors 122 include monochromatic detector, a multiple color detector (e.g., RGB detector), etc.

The light detecting elements 124 may be of any suitable size (e.g., 1-10 microns) and any suitable shape (e.g., circular, rectangular, square, etc.). For example, a CMOS or CCD light detecting element 220(*a*) may be 1-10 microns and an APD or PMT light detecting element 220(*a*) may be as large as 1-4 mm.

In some embodiments, the light detector 122 may be designed to improve the image quality of the SROFM 10. Due to the scattering angle of light 140 passing through the object 150 being imaged, projection image quality can be degraded if the object 150 being imaged is flowed away from the first surface 112(*a*) of the light detector 122. For this reason, the quality of images can be better for objects 150 with smaller thicknesses, especially for objects 150 in the size range of eukaryotic cells. In these embodiments, the light detector 122 may be designed without a color filter and microlens layer in order to decrease the acceptance angle of each pixel and the distance between the object 150 and the first surface layer 120 (i.e. the active sensing layer). Alternatively, if the light detector 122 (e.g., a CMOS sensor) was prefabricated with a color filter and a microlens layer, these components could be removed after fabrication in order to decrease the acceptance angle of each pixel and the distance between the object 150 and the first surface layer 120.

Light data refers to any suitable information related to the light received by the light detecting elements 124. For example, light data may include information about the properties of the light received such as the intensity of the light, the wavelength(s) of the light, the frequency or frequencies of the light, the polarization(s) of the light, the phase(s) of the light, the spin angular momentum(s) of the light, and/or other light properties associated with the light received by the light detecting element 124. Light data may also include the location of the receiving light detecting element(s) 124 in the two-dimensional array, the time that the light was received (sampling time), or other information related to the light received. In many embodiments, each light detecting element 124 can generate a signal with light data based on light received by the light detecting element 124.

A frame refers to light (image) data sampled at a specific sampling time (snapshot) by one or more light detecting elements 124 in the two dimensional array of the light detector 122. A sampling time refers to a specific time that the corresponding one or more light detecting elements 124 samples light data associated with light received. The light detector 122 samples one or more frames during the sampling process.

Each frame may be sampled by any suitable number and combination of light detecting elements 124 in the two-dimensional array ($A_{nm}$). For example, in a 4×4 two-dimensional array ($A_{n=4,m=4}$), the $A_{11}$, $A_{13}$, $A_{31}$, and $A_{33}$ pixels may be associated with a first frame ($F_1$), the $A_{12}$, $A_{14}$, $A_{32}$, and $A_{34}$ pixels may be associated with a second frame ($F_2$), the $A_{21}$, $A_{23}$, $A_{41}$, and $A_{43}$ pixels may be associated with a third frame ($F_3$), and the $A_{22}$, $A_{24}$, $A_{42}$, and $A_{44}$ pixels may be associated with a fourth frame ($F_4$). This series can be repeated for subsequent frames sampled.

In embodiments, the light detector 122 samples a sequence of n frames ($F_1, F_2, F_3, \ldots, F_n$) at a corresponding sequence of n sampling times ($t_1, t_2, t_3, \ldots t_n$). The sampling times are based on a sampling rate. Typically, the sampling rate is constant and can be described as the number of frames sampled per second, a typical sampling rate is 100 to 500 fps for a conventional light detector 122.

In most embodiments, one or more light detecting elements 124 sample a sequence of subpixel shifted frames ($SPF_1, SPF_2, SPF_3, \ldots, SPF_n$) at a sequence of n sampling times ($t_1, t_2, t_3, \ldots t_n$). The sequence of subpixel shifted frames is a sequence of frames sampled at sampling times based on a sub-pixel sampling rate. A subpixel sampling rate refers to a sampling rate where more than a single frame is being sampled as the object 150 moves a distance of a single light detecting element (pixel size). In these embodiments, the object(s) 150 being imaged moves a subpixel shift between neighboring frames ($F_i$ and $F_{i+1}$) being sampled. A subpixel shift refers to the translational movement of less than a pixel size. The corresponding N is greater than one in a subpixel sampling rate. For example, if a light detecting element 122 is a square pixel with a Δx of 5.2 microns (pixel size of 5.2 microns), the velocity V of the object is 10.4 microns/second, and the number of frames sampled over each pixel N is 100 (i.e. sub pixel sampling applies), the sub-pixel sampling rate, S=100×10.4 microns/second/5.2 microns=200 frames per second. In most cases, the SROFM 10 uses a subpixel sampling rate where the N is a non-integer number (e.g., N=1.2, 1.5, 1.6, 2.5, 5.2, 10.5, etc.).

Each frame sampled by the light detector 122 of embodiments includes snapshot image data that can be used to display a two dimensional, LR image of object(s) in the imaging area (e.g., an area where light passing through object(s) can be received by the light detector) of the fluid channel 122 during the sampling time. In some embodiments, the LR image may be a black and white image. In other embodiments, the LR image may be a color image. The resolution of a snapshot image is generally limited by the size of the light detecting elements 124 (e.g., pixel size) of the light detector 122 capturing the snapshot image. For example, an Aptina Inc.® MT9M001C12STM CMOS sensor chip has a pixel size of 5.2 micron and the snapshot image from this CMOS chip is about 5.2 micron.

Each sequence of n frames ($F_1, F_2, F_3, \ldots, F_n$) sampled by the light detector 122 of embodiments a corresponding sequence of n sampling times ($t_1, t_2, t_3, \ldots t_n$) includes image data that can be used to display a sequence of n LR images (LR Image$_1$, LR Image$_2$, LR Image$_3$, ... LR Image$_n$). Also, each sequence of n subpixel shifted frames ($SPF_1, SPF_2, SPF_3, \ldots, SPF_n$) can be used to display a sequence of n subpixel shifted images (SPSImage$_1$, SPSImage$_2$, SPSImage$_3$, ... SPSImage$_n$) refers to LR images generated by the n subpixel shifted frames sampled at a sequence of n sampling times ($t_1, t_2, t_3, \ldots t_n$) based on a sub-pixel sampling rate. The subpixel shifted images are LR images of the object 150 as it moves (shifts) a subpixel shift.

In many embodiments, the motion vector of one or more objects 150 is determined based on the sampled sequence of n frames (e.g., a sequence of subpixel shifted frames). A motion vector refers to the translational and/or rotational motion of an object 150 being imaged by the SROFM 10. Typically, the motion vector is determined as the translation and/or rotation of the object in terms of the local x'-axis and y'-axis of the two-dimensional array of light detecting elements 124.

In some embodiments, the motion vector can be determined using a motion estimation algorithm based on a sequence of n frames (e.g., a sequence of subpixel shifted frames). A motion vector estimation algorithm refers to a suitable algorithm for determining the motion vector of an object 150 being imaged based on the sequence of n frames. An example of a motion vector estimation algorithm is a subpixel-shift-motion estimation algorithm. Details of some exemplary motion estimation algorithms and other methods of determining a motion vector are described in Section IIA.

In many embodiments, HR image data and thus the corresponding HR image of an object 150 can be reconstructed using a SR algorithm from a sequence of subpixel shifted frames and a motion vector of the object. A HR image refers to a high resolution image (e.g., subpixel resolution image) based on HR image data reconstructed from a sequence of subpixel shifted frames and a motion vector. An example of the resolution of a HR image obtained by embodiments of the SROFM 10 is about 0.50 micron. A SR algorithm refers to an imaging processing technique that reconstructs image data for a single HR image from a sequence of lower resolution frames. An example of a SR algorithm is a shift-and-add pixel SR algorithm. Details of some exemplary SR algorithms are described in Section IIA.

In embodiments, one or more properties of the light 140 from illumination source(s) may change as the object(s) 150 being imaged moves through the imaging area of the fluid channel 112. The light 140 may have different properties at different sampling times in these embodiments. As an example, light 140 from different incidence angles may illuminate the fluid channel 112 at different sampling times. In some cases, light 140 provided by the illumination source(s) may be sequentially cycled through a series of different incidence angles. For example, at $t_1$ light 140 may have an incidence angle of $\theta_1$, at $t_2$ light 140 may have an incidence angle of $\theta_2$, at $t_3$ light 140 may have an incidence angle of $\theta_3$, at $t_4$ light 140 may have an incidence angle of $\theta_1$, at $t_5$ light 140 may have an incidence angle of $\theta_2$, etc. As another example, light 140 of different wavelengths may illuminate the fluid channel 112 at different sampling times. In some cases, the light 140 may be sequentially cycled through a series of different wavelengths as described above with respect to the series of incidence angles. Any suitable number of different incidence angles, wavelengths, and/or other light properties may be changed (n=1, 2, 3, 4, 5, etc.). Any suitable number of illumination sources may be used to provide the one or more properties of light 140 at the different sampling times.

The SROFM 10 of FIG. 1 also includes a host computer 200 communicatively coupled to the light detector 122. The host computer 200 comprises a processor 210 (e.g., microprocessor) coupled to a CRM 220. Alternatively, the host computer 200 can be a separate device. The host computer 200 can be any suitable computing device such as a smartphone.

The processor 230 executes code stored on the CRM 220 to perform some of the functions of SROFM 10 such as interpreting a sequence of n frames (e.g., a sequence of subpixel shifted frames) received in the one or more signals from the light detector 122, generating a sequence of n frames, generating reconstructed HR image data and corresponding image(s) from the sequence of n frames, generating SR color image data and corresponding SR color image(s) based on the sequence of frames, generating three-dimensional image data and three-dimensional images based on the sequence of frames, etc.

The processor 210 (e.g., microprocessor) can receive one or more signals with light data from the light detector 122 associated with the light received by the light detecting elements 124. For example, the processor 210 can receive one or more signals with light data in the form of a sequence of n frames (e.g., a sequence of subpixel shifted frames) sampled at a corresponding sequence of n sampling times ($t_1, t_2, t_3, \ldots t_n$). One or more LR images associated with the frames can be displayed.

In many embodiments, sampling times are based on a subpixel sampling rate. In these embodiments, the processor 210 can receive one or more signals with light data in the form of a sequence of subpixel shifted frames sampled at a corresponding sequence of n sampling times ($t_1, t_2, t_3, \ldots t_n$). One or more LR images associated with the subpixel shifted frames can be displayed.

The processor 210 can also determine a motion vector for one or more objects 150 based on the sequence of n frames (e.g., a sequence of subpixel shifted frames). The processor 210 can also reconstruct HR image data and HR image(s) of the object 150 using a SR algorithm and based on the sequence of frames (e.g., sequence of subpixel shifted frames) and the determined motion vector. In some cases, the reconstructed HR image of the object 150 is a high-resolution, black and white image. In other cases, the reconstructed HR image of the object 150 is a high resolution, color image.

In some embodiments, different wavelengths of light can be used at different sampling times to generate a multiple sequences of frames at a light detector 122. Each sequence of frames is associated with a different wavelength or color of light. The processor 210 can generate HR image data and HR images based on each sequence of frames associated with the corresponding wavelength. For example, three wavelengths of light (e.g., wavelengths associated with red, green, blue (RGB) colors) can be used to generate three sequences of frames, each frame associated with a different wavelength of light. The processor 210 can combine the image data from the different wavelengths of light to generate a multi-wavelength or multi-color image data (e.g., RGB color image data). The multi-wavelength or multi-color image data can be used to generate a multi-wavelength or multi-color image on a display 230.

In some embodiments, light of different incidence angles can be used at different sampling times to generate multiple sequences of frames of light data. Each sequence of frames is associated with a different incidence angle and a different view of the object(s) 150 being imaged. The processor 210 can generate HR image data and a HR image corresponding to each incident angle. In some cases, the processor 210 can generate SR three-dimensional image data and a SR three-dimensional image of the object(s) 150, using a tomography algorithm, based on multiple sequences of frames associated with different incidence angles. Any suitable a tomography algorithm can be used to compute three-dimensional image data and images from projection images from light 140 at different incidence angles. Some examples of suitable a tomography algorithm include filtered back-projection and iterative reconstruction.

The CRM (e.g., memory) 220 of embodiments stores code for performing some functions of the SROFM 10. The code is executable by the processor 210.

The CRM 220 of embodiments may include: a) code with a motion vector estimation algorithm 222 (shown in FIG. 1), b) code with a SR algorithm 224 (shown in FIG. 1), c) code with a tomography algorithm, d) code for interpreting light data (e.g., sequence of frames) received in one or more signals from the light detector 122, e) code for displaying a LR image based on image data in frame, f) code for generating SR two-dimensional image data (color or black and white) from a sequence of frames, g) code for generating a SR, three-dimensional image data from a plurality of SR two-dimensional image data associated with different incidence angles, h) code for displaying SR two-dimensional and/or three-dimensional images, i) and/or any other suitable code for performing functions of the SROFM 10. The CRM 220 may also include code for performing any of the signal processing or other software-related functions that may be created by those of ordinary skill in the art. The code may be in any suitable programming language including C, C++, Pascal, etc.

In FIG. 1, the CRM 220 comprises code with a motion estimation algorithm 222 and code with a pixel SR algorithm 224. Although the CRM 220 in FIG. 1 includes certain code, other code may also be included in CRM 220 or other embodiments. For example, the CRM 220 in FIG. 1 may include code with a tomography algorithm as well.

The SROFM 10 also includes a display 230 communicatively to the processor 210 to receive image data and provide output such as images to a user of the SROFM 10. Any suitable display may be used. For example, the display 230 may be a color display or a black and white display. In addition, the display 230 may be a two-dimensional display or a three-dimensional display. In one embodiment, the display 230 may be capable of displaying multiple views of an object 150.

Modifications, additions, or omissions may be made to SROFM 10 without departing from the scope of the disclosure. In addition, the components of SROFM 10 may be integrated or separated according to particular needs. For example, the processor 210 or other suitable processor may be integrated into the light detector 122 so that the light detector 122 performs one or more of the functions of the processor 210 in some embodiments. As another example, the processor 210 and CRM 220 may be components of a computer separate from the SROFM 10 and in communication with the SROFM 10. In another example, the processor 210 or other suitable processor may be integrated into the display 230 so that the display 230 performs one or more functions of the processor 210 in some embodiments.

A. On-Chip Design

In many embodiments, at least a portion of the body 110 of the SROFM 10 is in the form of a microfluidic chip (e.g., micromolded PDMS microfluidic chip) having one or more fluid channels 112. During fabrication, the microfluidic chip may be placed on top of the first surface layer 120 (e.g., PDMS layer) with the light detector 122 (e.g., CMOS sensor). In embodiments with multiple fluid channels 112, the SROFM 10 can perform parallel processing.

FIG. 2(a) is a schematic drawing of components of a SROFM 10 comprising a micromolded PDMS microfluidic chip bonded directly to a CMOS sensor, according to embodiments of the invention. In FIG. 2(a), the SROFM 10 includes a body 110 having a micromolded PDMS microfluidic chip with a straight portion 114 (shown in FIG. 2(c)) of a fluid channel 112 bonded directly to a light detector 122 (e.g., a CMOS sensor). The fluid channel 112 includes an inlet 160 and an outlet 170 connected to opposite ends of the fluid channel 112. The light detector 122 includes light detecting elements 124 in the form of a two-dimensional array. Although the illustrated embodiment shows a single fluid channel 112, other fluid channels 112 may be included in other embodiments to perform parallel processing.

In FIG. 2(a), the object 150 being imaged moves through the fluid channel 112 in the microfluidic chip. In the illustration, an illumination source (e.g., ambient light) provides light 140 from outside the microfluidic chip to the fluid channel 112 creating a projection image on the light detector 122 (e.g., CMOS sensor array).

FIG. 2(b) is a photograph of the body 110 of a SROFM 10 in the form of a microfluidic chip next to a quarter for scale, according to embodiments of the invention. In FIG. 2(b), the microfluidic chip includes a fluid channel 112 bonded over a light detector 122 (e.g., CMOS sensor). The microfluidic chip includes a fluid channel 112 having an inlet 160 and an outlet 170 on opposite ends of the fluid channel 112.

FIG. 2(c) is an image of a portion of the SROFM 10 of FIG. 2(a), according to embodiments of the invention. In FIG. 2(c), the SROFM 10 including a U-shaped fluid channel 112 in the body 110, and an inlet 160 and outlet 170 on opposite ends. The U-shaped fluid channel 112 includes three straight portions 114 and two curved portions 116.

B. Smartphone-Based SROFM

In some embodiments, the SROFM 10 may include a host computer 200 in the form of a smartphone or other mobile communication device, forming a smartphone-based SROFM 10. This smartphone-based SROFM 10 can be a portable, point-of-care and field diagnostic device. In some cases, this smartphone-based SROFM 10 can be used in remote diagnosis using a telemedicine system, where images taken from the patient end are transmitted to a centralized location. The doctors at the centralized location can make a diagnosis based on the images transmitted. In other cases, an automatic diagnosis system based on image recognition can be implemented on the smartphone-based SROFM 10, for example, as a smart-phone based application.

Although the host computer 200 in FIG. 1 is a smartphone, the host computer 200 in other embodiments may include another mobile communication device such as another cellular or wireless phone, personal digital assistant, portable computer, and the like. In one embodiment, the SROFM 10 may include a host computer 200 that is a USB-based mobile communication device to form a USB-based portable miniature microscope that can also be used as a portable, point-of-care and field diagnostic device in the same diagnostic systems. In some cases, the mobile communication device may be the illumination source.

Figure 3:
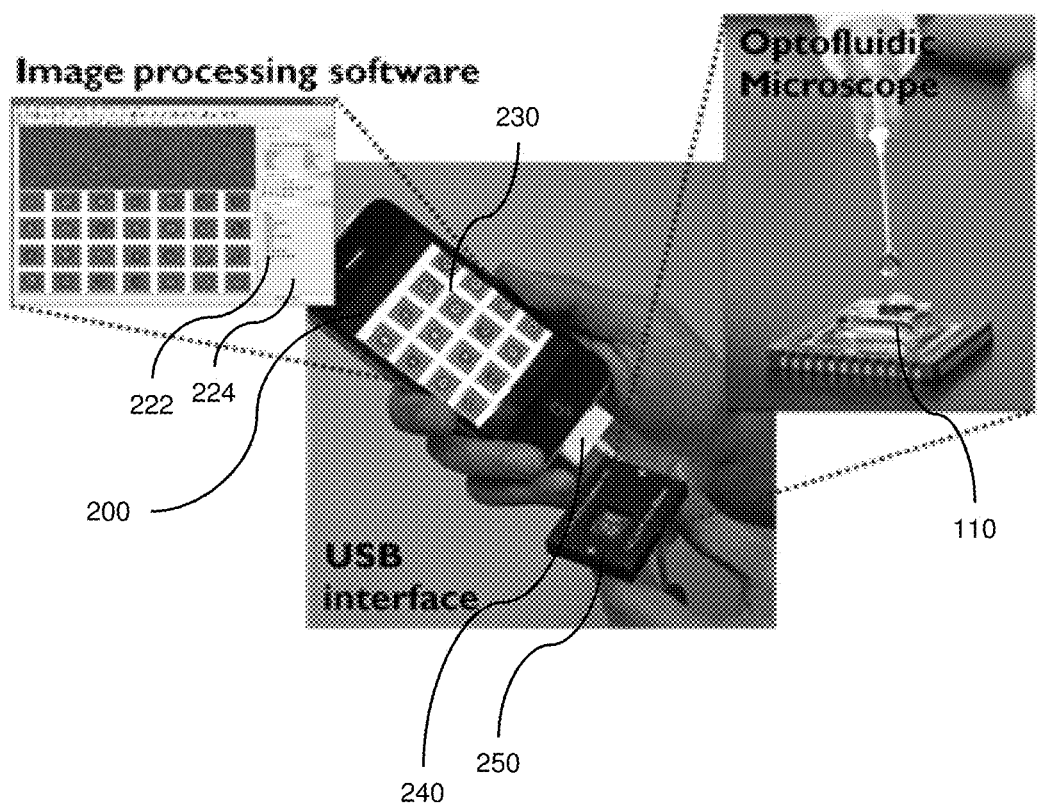
FIG. 3 is a series of images of a smartphone-based SROFM, according to an embodiment of the invention.

FIG. 3 is a series of images of a smartphone-based SROFM 10, according to an embodiment of the invention. In FIG. 3, the smartphone (i.e., host computer 200) has a processor 210 (not shown), a CRM 220 (not shown) including image processing software, and a USB interface 240. The image processing software includes code with a motion vector estimation algorithm 222 and code with a SR algorithm 224. In some cases, the image processing software may be in the form of a smartphone application.

In FIG. 3, the USB interface 240 is connected to an adaptor 250 for electronically coupling the processor 210 in the host computer 200 to the light detector 122 in the body 110 of the SROFM 10. In FIG. 3, the body 110 is in the form of a microfluidic chip. In this embodiment, the smartphone controls the light detector 122 and generates HR images from LR frames captured by the light detector 122 with the SR algorithm. A user of the smartphone can control image acquisition of the SROFM 10 using the touch screen and other control areas (e.g., buttons) on the smartphone.

A smartphone-based embodiment of the SROFM 10 may provide one or more technical advantages. One advantage may be that the smartphone-based SROFM 10 is a highly compact and simple design with a microfluidic chip that can be fabricated using standard semiconductor methods at a semiconductor foundry. The absence of bulk optics parts and the inclusion of planar design formats are compatible with semiconductor industry capabilities. Another advantage may be low cost. By exploiting economy-of-scale via semiconductor foundry manufacture, the microfluidic chip in the SROFM 10 can cost as little as $1 to make and can contain hundreds of fluid channels 112 in parallel on top of a light detector 122 to perform parallel image acquisition processes. Another advantage may be high throughput. Parallel processing through multiple fluid channels 112 in the same microfluidic chip allows us to boosts overall throughput. Given their cost and size advantages, multiple microfluidic chips can be operating in parallel to further increase throughput. Another advantage may be ease of sample localization and automated imaging implementation. Unlike other microscope methods, the flow of the fluid sample across the light detector 122 guarantees the detection of every bioentity of interest by the SROFM 10. The fluidic channel nature of the SROFM 10 also implies that there is never any need to perform view finding. Another advantage may be eliminating the microscope slide analysis step. The platform of the SROFM 10 is well suited for analyzing fluid samples. By cutting out the labor-intensive and skill-dependent step of slide analysis, the SROFM 10 represents a more streamline and straightforward microscopy analysis approach for fluid samples. In fact, the SROFM 10 represents a chip-scale fusion of the advantages of flow cytometry and microscopy imaging. Another advantage may be automatable image analysis and processing by the smartphone-based SROFM 10. As view finding and microscope focus adjustments are not required for a smartphone-based SROFM 10, it allows for automatic rejection of object images that are clearly true negatives and significantly cut down on the number of images that the clinicians would need to examine post-data processing. Another advantage may be elimination of the need for heavy equipment. A smartphone-based SROFM 10 may eliminate the requirement for a conventional microscope and the use of magnetic antibodies to process samples, which will eliminate the requirement for a centrifuge. Another advantage may be rapid diagnosis results. In some cases, the time of diagnosis may be reduced from the actual (10 min for processing of sample followed by 15 min of microscopic observation) to <1 min for the complete diagnosis procedure in a smartphone-based SROFM 10.

II. SROFM Image Processing

A. Introduction to Super Resolution (SR)

In some conventional imaging systems, the light detector is not sufficiently dense to meet the Nyquist criterion. Images taken by these light detectors have low resolution, being degraded by aliasing effects. An example of such a low resolution system is a conventional imaging device with a CMOS sensor. Due to noise constraints, CMOS pixel sizes are limited to anywhere between several to an order of magnitude times the size scale of the desired features of objects 150 (e.g., biological cells) being imaged. This large pixel size results in low resolution, pixilated images being generated since the CMOS sensor is sampling well below the spatial Nyquist rate of the sample. Other types of light detectors may afford better resolution, but do not come close in approaching the economy of scale of CMOS sensors, which are inexpensive and commonplace.

A SR (i.e. Super-resolution) technique can be used in some cases to help reduce the aliasing effect and enhance image resolution in these systems. Super-resolution is a general name given to imaging processing techniques that can reconstruct a single HR image from a sequence of lower resolution frames. An example of a SR technique can be found in Park, Sung Cheol, et al., "*Super-resolution image reconstruction: a technical overview*," IEEE Signal Processing Magazine, pp. 21-36 (2003), which is hereby incorporated by reference in its entirety for all purposes. The general principle of SR techniques involves taking a low resolution frame sequence in which the target object is sampled at below the Nyquist rate, where subsequent frames involve a sub-pixel translational shift. That is, the sequence of low resolution frames is sampled at a subpixel sampling rate. An example of technique for reconstructing a HR image from a sequence of rotated and translated frames can be found in Hardie, Russell C., et al., "*High resolution image reconstruction from a sequence of rotated and translated frames and its application to an infrared imaging system*," Optical Engineering, (1997), which is hereby incorporated by reference in its entirety for all purposes. If the translational shift is known, then a system of matrix equations can be established from the low resolution sequence to solve for sub-pixel values to create a single reconstructed HR image. In general, the original HR image can theoretically be recovered even from a significantly decimated, blurred, translated, and rotated LR image sequence; resolution is limited only by the diffraction limit and noise, as described in Park, Sung Cheol, et al., "*Super-resolution image reconstruction: a technical overview*," IEEE Signal Processing Magazine, pp. 21-36 (2003).

Some examples of conventional SR algorithms can be found in Gillette, J., et al., "*Aliasing reduction in staring infrared imagers utilizing subpixel techniques*," Optical Engineering, Vol. 34, p. 3130 (1995), Farsiu, S., et al., "*Fast and robust multiframe super resolution*," IEEE Transactions on Image Processing, vol. 13, pp. 1327-1344 (2004), Bishara, W., et al., "*Lensfree on-chip microscopy over a wide field-of-view using pixel super-resolution*," Optics Express, Vol. 18, pp. 11181-11191 (2010), and Shi, J., et al., "*Small-kernel superresolution methods for microscanning imaging systems*," Applied Optics, Vol. 45, pp. 1203-1214 (2006), which are hereby incorporated by reference in their entirety for all purposes. The HR image-restoration of these SR algorithms relies on the relative subpixel motion between the LR images, and in this case, a unique 'look' at the scene is provided by each frame.

Conventional SR algorithms use an uncontrolled or a controlled SR microscanning scheme. In an uncontrolled SR microscanning scheme, during image acquisition, a camera can be fixed to look at a moving object or the camera can be mounted on a moving platform (such as holding a camera in a hand) to look at a fixed object. An example of uncontrolled SR microscanning scheme can be found in Gillette, J., et al., "*Aliasing reduction in staring infrared imagers utilizing subpixel techniques*," Optical Engineering, Vol. 34, p. 3130 (1995). It is also possible to introduce a controller and actuator to precisely control the relative subpixel motion of the LR image sequence, and this is referred to as controlled SR microscanning. Examples of controlled SR microscanning schemes can be found in Gillette, J., et al., "*Aliasing reduction in staring infrared imagers utilizing subpixel techniques*," Optical Engineering, Vol. 34, p. 3130 (1995), Bishara, W., et al., "*Lensfree on-chip microscopy over a wide field-of-view using pixel super-resolution*," Optics Express, Vol. 18, pp. 11181-11191 (2010), and Shi, J., et al., "*Small-kernel superresolution methods for microscanning imaging systems*," Applied Optics, Vol. 45, pp. 1203-1214 (2006).

The SROFM 10 uses a semi-controlled SR microscanning scheme based on integrating a fluid channel 112 with a two-dimensional array of light detecting elements 124 (e.g., a CMOS sensor). In general, the subpixel movement of microscopic object(s) between frames sampled by an SROFM 10 can be considered semi-controlled because the movement of the microscopic object(s) is based on a controllable fluid flow and a controllable particulate transport in part due to being confined by the geometry of a fluid channel 112. For example, the height of the fluid channel 112 can be designed to maintain the object(s) 150 near the first surface layer 120 of the light detector 122, which can improve the quality of images of the microscopic object(s) captured by the SROFM 10. The semi-controlled SR microscanning scheme of the SROFM 10 allows for the reconstruction of HR images of microscopic object(s) 150 from the sequence of LR frames sampled by a light detector including sparse light detectors.

In the semi-controlled scheme used by the SROFM 10, an object 150 being imaged flows through the fluid channel 112 over the two-dimensional array of light detecting elements 124. The light detector 122 records a frame at every subpixel movement of the object 150. Individually, each frame can be used to generate an LR image where resolution is limited to the size of the light detecting elements 124 (i.e. pixel size) and the light detecting elements 124 are large. As the object 150 moves across the light detector 122, a sequence of LR frames of the object 150 is recorded and then used to reconstruct an anti-aliasing HR image of the object 150 with an SR algorithm. Some details of a semi-controlled SR microscanning scheme used in a SROFM 10 can be found in Zheng, G., et al., "*Sub-pixel resolving optofluidic microscope for on-chip cell imaging*," Lab Chip, Vol. 10, pp. 3125-3129 (2010), which is hereby incorporated by reference in its entirety for all purposes.

The HR image restoration of many SR algorithms largely depends on the knowledge of the precise subpixel shifts of object(s) in the LR images, collectively termed the motion vector of the LR image sequence. For the conventional uncontrolled SR microscanning case, however, it is difficult to accurately estimate such a subpixel motion; therefore, it puts a practical limit on the performance of SR algorithms. An example of the limits on performance of SR algorithms can be found in Lin, Z., and Shum, H., "*Fundamental limits of reconstruction-based superresolution algorithms under local translation*," IEEE Transactions on Pattern Analysis and Machine Intelligence, pp. 83-97 (2004), which is hereby incorporated by reference in its entirety for all purposes. For the conventional controlled microscanning case, expensive motion controller and actuator are often involved. In addition, precise step-by-step scanning within the subpixel limitation can be time-consuming.

In the semi-controlled SR microscanning scheme used by the SROFM 10, the motion vector can be easily and accurately determined, allowing for high quality HR image restoration. In the SROFM 10, the motion vector is determined by analyzing an approximate position of an object across the LR image sequence. The motion vector is easily analyzed in a SROFM 10 because the flow rate is highly stable within the fluid channel 112 (i.e. low Reynolds number). For an object moving at a constant speed, the motion vector can be calculated from the location of the object 150 in the first and last images in the sequence. However, in many cases, the motion of the object 150 is not uniform or purely translational due to the geometry of the object itself, defects in the microfluidic channel 112, and/or change in the flow rate. To compensate for this non-uniform motion, a motion vector estimation algorithm can be used to accurately estimate the motion vector from the sequence of LR images. Some examples of such motion estimation algorithms can be found in Zheng, G., et al., "*Supplementary Information for: Sub-pixel resolving optofluidic microscope for on-chip cell imaging*," Lap Chip, Vol. 10 (2010), which is hereby incorporated by reference in its entirety for all purposes.

In one motion vector estimation algorithm, first the background of each LR image is subtracted and contrast enhanced. Highly scattering objects in LR images appear darker than the background, thus this information can be used to determine the location of the object within each LR frame. To do this, the image is binarized using a single threshold computed from the entropy of the image histogram. An example of binarizing an image can be found in Kapur, J., et al., Computer vision, graphics, and image processing, 29, pp. 273-285 (1985). The geometric centroid of each of these binarized images from the LR image sequence is then computed and the entire array of centroids is low pass filtered to account for both the smooth flow pattern of the sample and the quantization error from binarizing and computing the centroid of each individual LR image.

For samples with lower contrast or bright spots, the motion vector is calculated in a similar manner, except the images are binarized with two thresholds. The background noise level is calculated and the image binarized by converting any pixel that is a certain amount above or below the noise level to 0 while making the rest 1. Also, in order to avoid errors due to the geometry of the object 150, the algorithm uses the pixel coordinate of the bounding box of the object 150 and low pass filter the data to obtain sub-pixel shift values. For objects 150 (e.g.; microspheres) that are smaller than a pixel size, it is more difficult to distinguish a pixel response that results from the shadowing of the object 150 from the sensor's background noise. In this case, the motion vector is obtained by observing the blinking of the pixels on the expected pathway of objects 150 (parallel to the channel wall). From the raw data, the pixel coordinates are obtained where the objects are expected to flow through. This pathway can be any line of pixels within the fluid channel 112 that are parallel to the channel wall, since the objects 150 follow the laminar flow of the solution. The algorithm extracts the time variation of the pixel response on the pathway, which shows the blinking of the pixels as the object 150 moves across each pixel, and calculates the motion vector from the slope ($\Delta x/\Delta f$, $\Delta y/\Delta f$).

B. Some Technical Advantages of Using a SROFM

The semi-controlled SR microscanning scheme used by the SROFM 10 may provide one or more technical advantages over conventional SR microscanning schemes. An advantage over conventional uncontrolled SR microscanning schemes may be that, unlike conventional uncontrolled SR microscanning schemes, the motion of the object in the present scheme can be controlled by pressure driven flow or other fluid flow or particulate transport technique in the microfluidic channel. An advantage over conventional controlled SR microscanning schemes is that the present scheme takes advantage of motion damping effects of the fluid flow, which can result in more accurate subpixel motion vector estimation. Another advantage over conventional controlled SR microscanning schemes is that the present scheme does not involve using an expensive motion controller and actuator.

The SROFM 10 may provide one or more technical advantages over conventional OFM devices, as well. One advantage may be that since the SROFM 10 does not rely on moving across an aperture array or photosensor array to acquire images, the time used to capture the object images can be 100 times shorter than the conventional OFM and the throughput of SROFM 10 can be about 100 times higher than the conventional OFM. Another advantage may be that the resolution limit of the SROFM 10 is about 0.5 micron, which is higher than 0.85 micron of the conventional OFM. Another advantage may be that since the SROFM 10 can correct the rotation effect of the object, the image yield of SROFM 10 is almost 100%, which is about 10 times higher than the conventional OFM (the yield of the conventional OFM is limited by the rotation of the object, and it is about 10%). Another advantage may be that the SROFM can image the object rotation in the fluid channel, which can be difficult for a conventional OFM. Another advantage of the SROFM 10 is that it can generate three-dimensional images of the object. An example of a conventional OFM device can be found in Cui, X., et al., "*Lensless high-resolution on-chip optofluidic microscopes for Caenorhabditis elegans and cell imaging,*" Proceedings of the National Academy of Sciences, Vol. 105, p. 10670 (2008).

In addition, the SROFM 10 provides numerous advantages over conventional high resolution microscopes. For example, the SROFM 10 eliminates the need for large, bulky or expensive optical components of a conventional high resolution microscope. The SROFM 10 can acquire HR images with a simple, inexpensive design that integrates a fluid channel 112 over a light detector 112, with a software-based signal processing component (e.g., processor 210) that can generate HR image data from a sequence of LR frames taken at a subpixel sampling rate. The light detector 112 samples frames at a high sampling rate (e.g., subpixel sampling rate) in the time domain to compensate for low sampling of projection images in the spatial domain, since spatial resolution is limited by pixel size.

C. SR Imaging of SROFM

Generally, the SROFM 10 uses a high sampling rate (e.g., subpixel sampling rate) in the time domain to offset the sub-Nyquist rate sampling in the spatial domain of the projection images, combining work done in super resolution imaging with optofluidic microscopy to provide a simple, low cost, high throughput microscopy device with significant resolution enhancement.

The SROFM 10 has a fluid flow carrying an object 150 being imaged through the fluid channel 112 and across the light detector 122 (e.g., CMOS sensor array). Light 140 provided to the fluid channel 112 creates projection images on the light detector 122 (e.g., CMOS sensor array). As the object 150 moves through the fluid channel 112, the light detector 122 samples a sequence of subpixel shifted LR frames at a subpixel sampling rate. A subpixel shift refers to the movement of the object 150 being imaged of less than a size of the light detecting element 124 (pixel).

Typically, the two-dimensional array of light detecting elements 124 is oriented at an angle α (shown in FIG. 1) with respect to the longitudinal axis of the fluid channel 112. By oriented the two-dimensional array at an angle, an object 150 moving with the fluid flow generally along the longitudinal axis of the fluid channel 112, translates in both the x'-direction and y'-direction of the local axes of the two-dimensional array of light detecting elements 124. Although any angle can be used, typically the angle ranges from 10-30 degrees to maintain sufficient displacement along the y'-direction for HR image reconstruction using a SR algorithm and to maximize the frame sampling rate by using fewer pixel rows in the imaging area of interest.

Raw-images based on the sequence of subpixel-shifted frames show direct-projections of the object 150 that are pixelated according to the pixel size of the light detector 122. Since the subpixel shifted frames can be acquired at a high frame sampling rate (e.g., subpixel sampling rate), the imaged object 150 has sub-pixel displacements (shifts) between subsequent frames within the sequence, allowing for the use of SR algorithms to recover (reconstruct) an anti-aliased reconstructed HR image. The resolution of raw-images based on the sequence of subpixel-shifted frames taken by the light detector 122 is generally based on pixel size. For example, an Aptina Inc.® MT9M001C12STM CMOS chip has a pixel size of 5.2 micron and the resolution of a projection image produced by this sensor chip is about 5.2 micron.

The sequence of subpixel shifted LR (sub-sampled) frames are taken at a high enough rate such that multiple frames are taken in between object movements of a pixel length. The sequence of sub-sampled, low resolution frames can be used to generate a high-resolution, two-dimensional image of the projection using SR techniques (algorithms). This HR image of the projection can further be deconvolved with the point spread function of the optical system to recover a focused image of the object 150.

The SROFM 10 can use any suitable SR algorithm to reconstruct one or more HR images from the sequence of subpixel shifted frames of direct projections on the light detector 122 of an object 150 in a fluid flow moving through a fluid channel 112. The sequence of subpixel shifted frames used in this HR image reconstruction have a subpixel shift in neighboring frames to provide new information to the HR image. The subpixel shift can be easily maintained between sampling times by taking the sequence of frames while flowing the fluid sample with the object 150 through the fluid channel 112 (e.g., a PDMS microfluidic channel) over a two-dimensional array of light detecting elements 124 (e.g., a CMOS image sensor).

Figure 4:
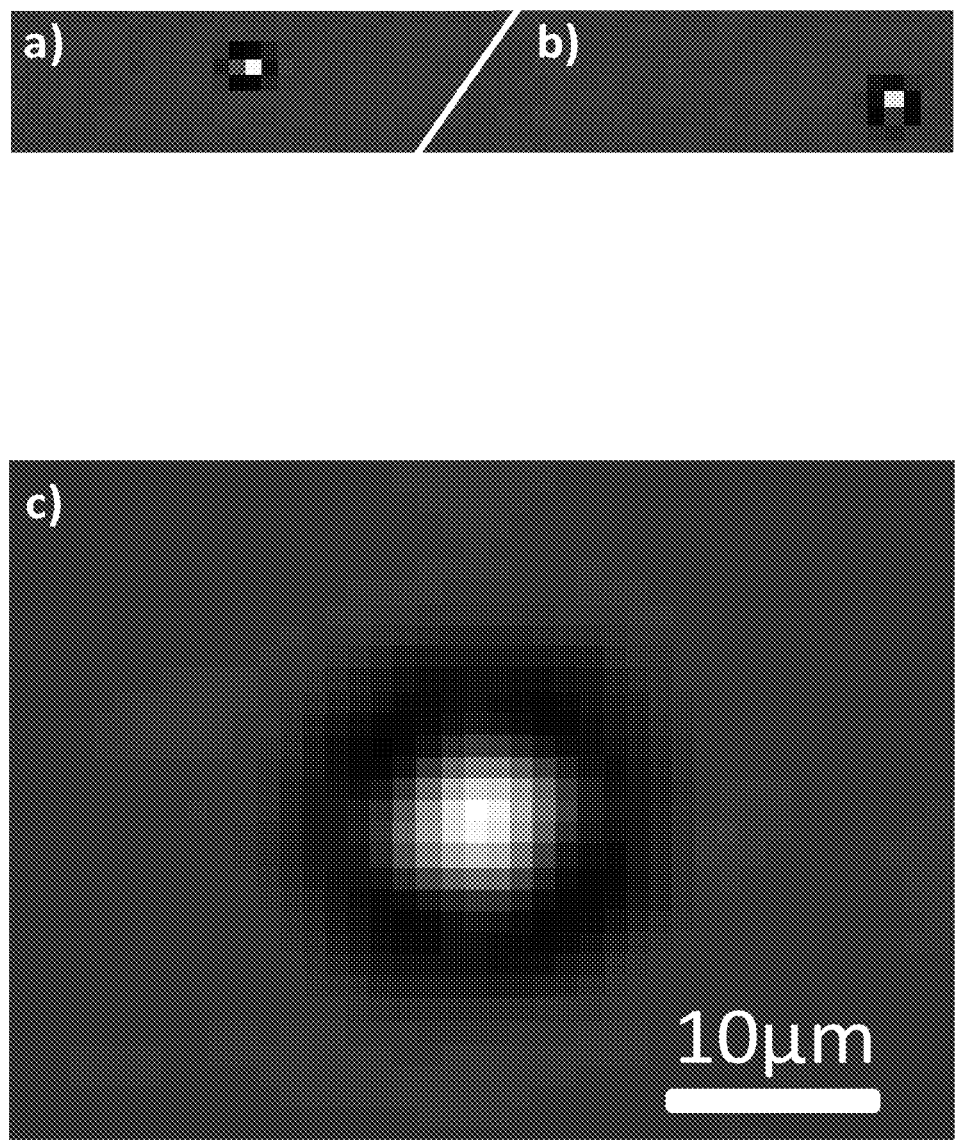
FIG. 4(a) is a first low resolution (LR) image based on a first frame taken at a first sampling time that is produced by a CMOS chip, according to embodiments of the invention.
FIG. 4(b) is a second LR image based on a second frame taken at a second sampling time that is produced by the CMOS chip of FIG. 4(a), according to embodiments of the invention.
FIG. 4(c) is a reconstructed high resolution (HR) image based on the first frame and second frames of FIGS. 4(a) and 4(b) and reconstructed using a super resolution (SR) algorithm, according to embodiments of the invention.

FIG. 4(*a*) is a first LR image based on a first frame taken at a first sampling time that is produced by a that is produced by an Aptina Inc.® MT9M001C12STM CMOS chip, according to embodiments of the invention. FIG. 4(*b*) is a second LR image based on a second frame taken at a second sampling time that is produced by the Aptina Inc.® MT9M001C12STM CMOS chip of FIG. 4(*a*), according to embodiments of the invention. FIG. 4(*c*) is a reconstructed HR image based on the first frame and second frames of FIGS. 4(*a*) and 4(*b*) and reconstructed using a SR algorithm, according to embodiments of the invention. An enhancement factor (resolution improvement) of 8 has been applied to the reconstruction, and as such, a single pixel of the image is 5.2/8=0.65 micron.

Furthermore, this super resolution imaging concept can be extended beyond two dimensions. Computed tomography using different incident angles of light to generate multiple projections can be used to create a three-dimensional reconstruction of an image of the object 150. An example of using computed tomography to generate a three-dimensional image of an object can be found in Miao, Qin, et al., "*Dual-modal three-dimensional imaging of single cells with isometric high resolution using an optical projection tomography microscope,*" Journal of Biomedical Optics, Vol. 14 (2009), which is hereby incorporated by reference in its entirety for all purposes. The SROFM 10 may use any suitable tomographic reconstruction algorithm to reconstruct a three-dimensional image of the object 150.

D. General Operation of SROFM

During general operation of the SROFM 10, a fluid specimen with object(s) 150 being imaged moves through the fluid channel 112 and across the two-dimensional array of light detecting elements 124 of the light detector 122. Light 140 from one or more illumination sources is provided to the fluid channel 112. The light detector 122 samples a sequence of subpixel shifted frames taken at a subpixel sampling rate. The processor 210 uses a motion estimation algorithm to estimate a motion vector of the object(s) 150. The processor 210 reconstructs one or more HR images of the object(s) 150 based on the motion vector and the sequence of subpixel shifted frames.

In some embodiments, a fluid specimen containing an adequate concentration of the object(s) 150 is introduced into the fluid channel 112 through an inlet 160. Any technique for fluid flow or particulate transport can be used. For example, fluid flow may be induced by the capillary action and pressure difference between the inlet 160 and outlet 170, delivering the object(s) 150 through the imaging area above the two-dimensional array of light detecting elements 124 of the light detector 122 (e.g., CMOS sensor). In some cases, the fluid channel 112 is sized to keep the object(s) 150 being imaged in an imaging area close to the first surface 112(*a*) of the light detector 122.

As the object(s) moves through the fluid channel 112, light 140 from one or more illumination sources illuminates the fluid channel 112 generating projections on the light detector 122. The light detector 122 captures a sequence of LR frames at a subpixel frame sampling rate. A sequence of LR images can be generated with the sequence of LR frames.

Any flow rate, subpixel frame sampling rate, and field-of-view (FOV) can be used that will generate a suitable sequence of LR frames for reconstructing HR image data and a corresponding HR image using a SR algorithm. In one example, the object(s) 150 was imaged at a flow speed of 200 μm/s, with a subpixel frame sampling rate of 500 fps and a field-of-view (FOV) of 250 μm by 3 mm. The flow rate of the fluid specimen, and hence our throughput, can be further increased with a smaller FOV and higher subpixel frame sampling rate. In one example, 50 LR frames (50 LR images) were enough to create a HR image with a resolution enhancement factor of 7 indicating that with a maximum subpixel frame sampling rate of 50000 fps and FOV of 50 μm by 100 μm, a continuous stream of objects 150 can be imaged at a rate of 1000 images/sec, with each image possibly containing multiple objects 150 (e.g., cells). The ultimate limit of throughput in a SROFM 10 is the frame sampling rate of the light detector 122. Thus, to increase throughput of the SROFM 10, light detectors with high speed shutters can be used. Some examples of high speed global-shutter CMOS image sensors are the Aptina MT9M001 and Aptina MT9T001 CMOS sensors. Some high speed shutter light detectors (e.g., Aptina MT9M001 and Aptina MT9T001) may have ten times the frame sampling speed of other light detectors (e.g., Aptina MT9V403). The high frame sampling rate of these high speed shutter light detectors 122 and the integration with a microfluidic system may allow for high-throughput on-chip scanning of biological samples and other fluid specimens with high resolution imaging capabilities.

When using multi-frame pixel SR techniques, accurate determination of the motion vector of object(s) 150 can be important for high quality restoration. In a SROFM 10, the subpixel shifts can be determined by examining the movement of objects in the sequence of LR frames. For an object 150 moving at constant speed, the motion vector can be calculated from the location of the object 150 in the first and last LR images. However, in many cases, the motion is not uniform or purely translational due to the geometry of the object itself, defects in the microfluidic channel 112, and/or change in the flow rate. To compensate for this non-uniform motion, the SROFM 10 uses a motion vector estimation algorithm to estimate the motion vector from the sequence of LR frames. Some examples of such motion estimation algorithms can be found in Zheng, G., et al., "*Supplementary Information for: Sub-pixel resolving optofluidic microscope for on-chip cell imaging*," Lap Chip, Vol. 10 (2010). Some details of such motion estimation algorithms are described in Section IIA above.

Once a sequence of frames is captured by the SROFM 10, the processor 210 can determine the motion vector of the object(s) being imaged from the sequence of LR frames. With the sequence of frames and the determined motion vector, the processor 210 can use a SR algorithm to obtain one or more HR images of the object(s) 150. An example of a SR algorithm that can be used is the shift-and-add reconstruction algorithm, which can be found in Farsiu, S., et al., "*Fast and robust multiframe super resolution*," IEEE Transactions on Image Processing, Vol. 13, pp. 1327-1344 (2004), or Elad M., and Hel-Or, Y., "*A fast super-resolution reconstruction algorithm for pure translational motion and common space-invariant blur*," IEEE Transactions on Image Processing, Vol. 10, pp. 1187-1193 (2001), which are hereby incorporated by reference in their entirety for all purposes.

The raw LR images (e.g., frames) from the light detector 122 can be considered a subsampled (i.e. aliased) version of the original image, with a sampling frequency corresponding to the pixel size. In each frame, the object 150 is shifted from the previous frame with a small subpixel displacement which can be estimated from the speed of the object across the sequence of LR images (e.g., the motion vector).

In a reconstruction process using a shift-and-add SR algorithm, an HR image grid is formed with an enhancement factor of n, where each n-by-n pixel area of the HR image grid corresponds to a 1-by-1 pixel area of the LR frame grid. Then, the HR image grid is filled with the corresponding LR pixel values based on the sequence of LR frames. The mapping of the pixels within the n-by-n grid is determined from the known, estimated sub-pixel shift of each image. In other words, each LR image is shifted by the relative sub-pixel shift of the object from its original position and then added together to form a HR image. Finally, deblurring using the wiener deconvolution method is used to remove blurring and noise in the final image.

Figure 5:
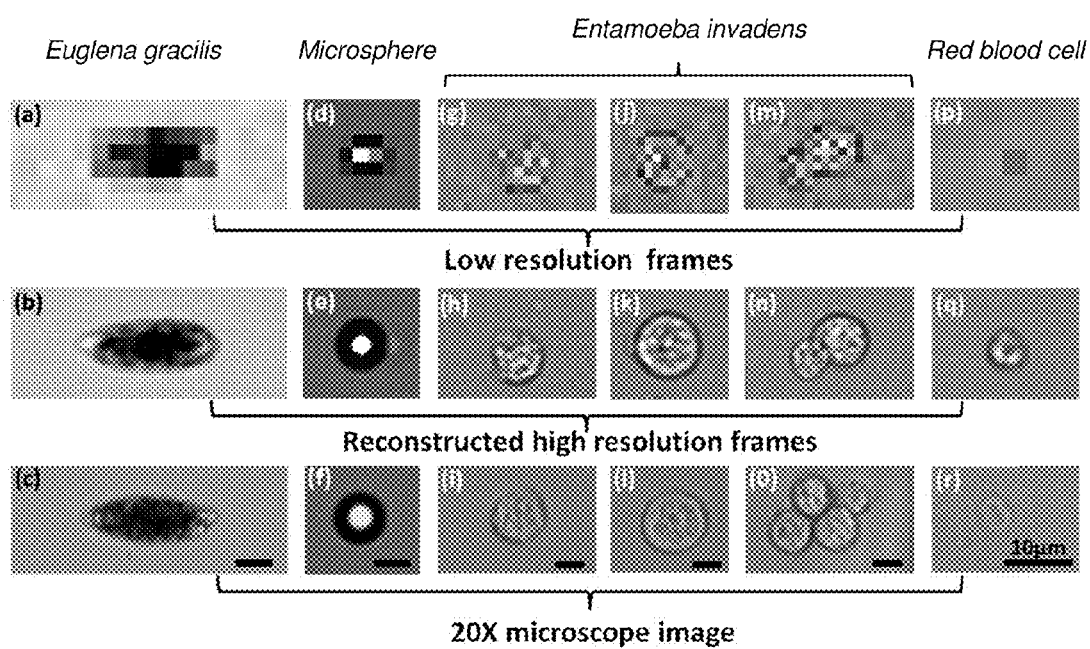
FIG. 5 is a comparison of images generated by a SROFM of embodiments of the invention, and images generated by a conventional microscope with a 20× objective lens.

FIG. 5 shows a comparison of images generated by a SROFM 10 of embodiments of the invention, and images generated by a conventional microscope with a 20× objective lens. FIGS. 5(*a*), (*d*), (*g*), (*j*), (*m*), and (*p*) are raw LR images of microscopic objects obtained from a SROFM 10, according to embodiments of the invention. FIGS. 5(*b*), (*e*), (*h*), (*k*), (*n*), and (*q*) are HR images of microscopic objects obtained by the SROFM 10, according to embodiments of the invention. The HR images were reconstructed from a sequence of 40 to 50 LR frames. FIGS. 5(*c*), (*f*), (*i*), (*l*), (*o*), and (*r*) are images of microscopic objects obtained by a conventional microscope with a 20× objective lens. The microscopic object shown in FIGS. 5(*a*), 5(*b*), and 5(*c*) is a protist *Euglena gracilis* (d~15 μm). The microscopic object shown in FIGS. 5(*d*), 5(*e*), and 5(*f*) is a 15 μm microsphere. The microscopic object shown in FIGS. 5(*g*), 5(*h*), and 5(*i*) is an *Entamoeba invadens* cyst (d~25 μm). The microscopic object shown in FIGS. 5(*j*), 5(*k*), and 5(*l*) is an *Entamoeba invadens* cyst (d~25 μm). The microscopic objects shown in FIGS. 5(*m*), 5(*n*), and 5(*o*) are *Entamoeba invadens* cysts (d~25 μm). The microscopic object shown in FIGS. 5(*p*), 5(*q*), and 5(*r*) is a mice red blood cell (d~5 μm). The pixel sizes of the light detectors used in the SROFM 10, and hence the resolution limit of the LR images, was 5.2 μm for the *Euglena* and microsphere, and 3.2 μm for the *Entamoeba* and mice red blood cell. The HR images were obtained with a resolution enhancement factor of 10. Note that each individual LR image contains very little spatial information about the object(s) other than its location and rough size. The images obtained by the SROFM 10 and shown in FIGS. 5(*b*), (*e*), (*h*), (*k*), (*n*), and (*q*) are comparable to conventional microscope images taken with 20× objective lens shown in FIGS. 5(*c*), (*f*), (*i*), (*l*), (*o*), and (*r*).

Figure 6:
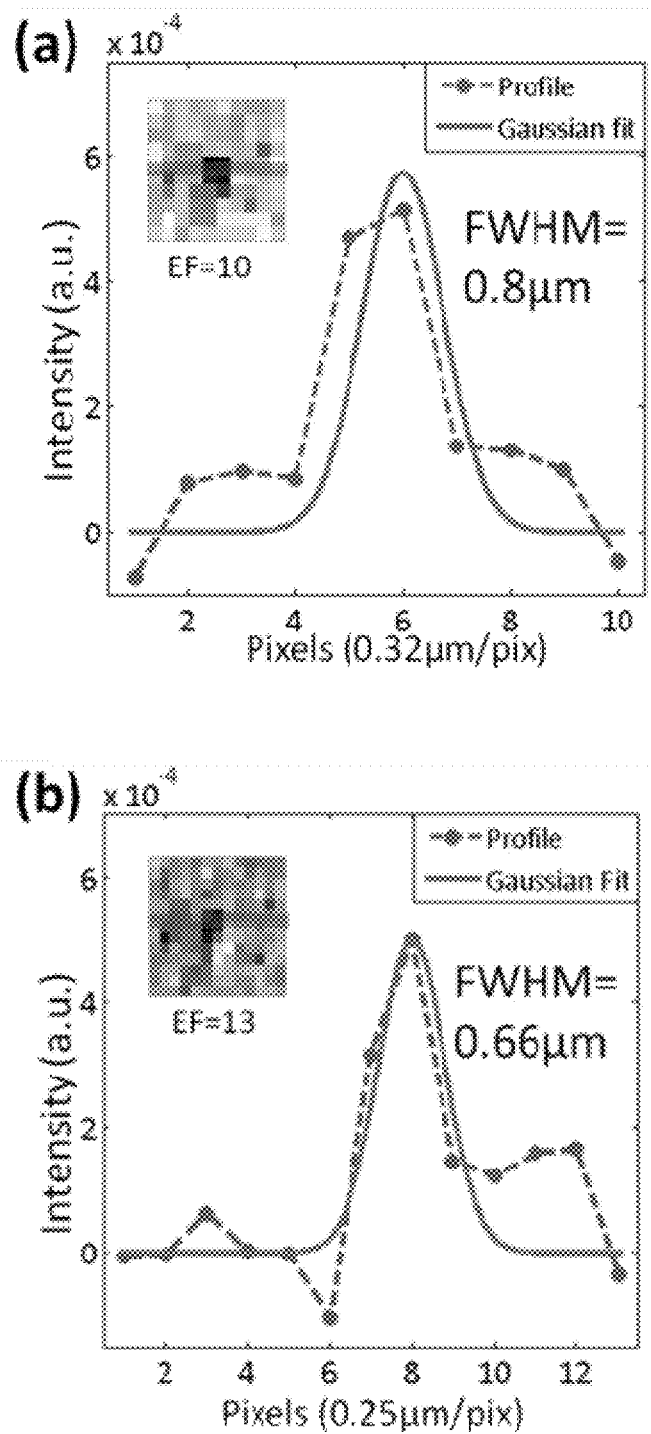
FIG. 6(a) is a reconstructed high resolution image of a 0.5 μm microsphere with the enhancement factor of 10 and a corresponding intensity profile of the 0.5 μm microsphere from the reconstructed HR image, according to an embodiment of the invention.
FIG. 6(b) is a reconstructed HR image of a 0.5 μm microsphere with the enhancement factor of 13 and a corresponding intensity profile of the 0.5 μm microsphere from the reconstructed HR image, according to an embodiment of the invention.

To establish the extent of resolution improvement in increasing the resolution enhancement factor and the resolution limit, a fluid specimen of a solution of 0.5 µm microspheres was imaged by a SROFM 10 of an embodiment. FIG. 6(*a*) is the reconstructed HR image of a 0.5 µm microsphere with the enhancement factor of 10 and a corresponding intensity profile of the 0.5 µm microsphere from the reconstructed HR image, according to an embodiment of the invention. FIG. 6(*b*) shows the reconstructed HR image of a 0.5 µm microsphere with the enhancement factor of 13 and a corresponding intensity profile of the 0.5 µm microsphere from the reconstructed HR image, according to an embodiment of the invention. The centers of these microspheres can clearly be resolved and identified with the full with half maximum of 0.80 µm and 0.65 µm. The FWHMs of the intensity profiles in FIG. 6(*a*) and FIG. 6(*b*) are 0.8 µm and 0.66 µm, respectively. The second data set based on an enhancement factor of 13, implies that the SROFM 10 of this embodiments has a resolution limit of ~0.75 µm (adjacent particles can be resolved as long as they are 3 or more SR pixels apart). A more detailed study of the resolution limit with different sample-to-floor separations can be measured with a near-field scanning optical microscope (NSOM).

E. Operating Schemes

In many embodiments, the fluid specimen is flowed directly (several microns) above a light detector (e.g., a high speed CMOS sensor) with illumination 140 from the top. As object(s) being imaged move through the fluid channel 112, the light detector 122 samples a sequence of subpixel shifted frames that can be used to create a sequence of "pixelated" LR images. The processor 210 can use a SR technique to combine two or more subpixel shifted frames to create a smaller sequence of HR images. An examples of such a SR technique can be found in Schultz, Richard, et al. "Subpixel motion estimation for super-resolution image sequence enhancement," Journal of Visual Communication and Image Representation, 9, Issue 1, (March 1998), which is hereby incorporated by reference in its entirety for all purposes.

The general operating principle of the SROFM 10 involves sampling the sequence of subpixel shifted frames at below the Nyquist rate and for which subsequent frames involve a slight subpixel translational shift. If the translational shift is known, then a system of matrix equations can be established from the subpixel shifted frames to solve for subpixel values to create HR image data for one or more HR images. In general, the original HR image can theoretically be recovered even from a frame sequence associated with a significantly decimated, blurred, translated, and rotated LR images. Resolution of the HR images of embodiments is limited only by the diffraction limit and noise.

Various operating schemes can be used by embodiments of the SROFM 10. Some examples of the operating schemes used by the SROFM 10 of embodiments are described below.

Scheme 1—Monochromatic Two-Dimensional SROFM

In a first scheme, a SROFM 10 of embodiments can reconstruct one or more SR monochromatic, two-dimensional images of the object(s) 150 from a sequence of subpixel shifted frames captured by a monochromatic light detector 122 and the motion vector. The motion vector describes the translational shift of the object 150 and can be estimated using a motion estimation algorithm. Each subpixel shifted frame corresponds to an LR projection image.

For the case specific to the SROFM 10, there is only the known translational shift and space invariant point spread function of the system, H, which is also known. Hence more effective and computationally efficient SR techniques can be applied such as the SR technique described in Elad M., and Hel-Or, Y., "*A fast super-resolution reconstruction algorithm for pure translational motion and common space-invariant blur*," IEEE Transactions on Image Processing, Vol. 10, pp. 1187-1193 (2001), which is hereby incorporated by reference in its entirety for all purposes.

The desired output of the SROFM 10 is the image data of the original (high resolution) image, X, of the object 150. For the image data of the original (high resolution) image, X, of an object, the sequence of LR frames of the object:

$$\{Y_k = D_k H F_k X + V_k\} \quad \text{(Eqn. 1)}$$

can be obtained, where $F_k$ is the translational shift, H is the point spread function of the optical system, $D_k$ is the downsampling of the original image data and $V_k$ is white noise with auto-correlation $W_k = E\{V_k V_k^T\}$.

Hence, by minimizing the least square error, the computed HR image data $\hat{X}$ can be obtained from the sequence of N LR frames as follows:

$$\hat{X} = \underset{X}{\text{ArgMin}} \left\{ \sum_{k=1}^{N} [Y_k - D_k H F_k X]^T W_k^{-1} [Y_k - D_k H F_k X] \right\} \quad \text{(Eqn. 2)}$$

This optimization can be easily done computationally with a close form formula. The end result of this optimization is image data for an in-focus HR image of the object(s) 150 generated from the LR frames captured by the light detector 122.

Scheme 2—Color Two-Dimensional SROFM

In a second scheme, the SROFM 10 includes a color light detector 112 (e.g., a color CMOS sensor) that can capture a sequence of subpixel shifted color frames that could be used to display a sequence of color LR images. The processor 210 can generate one or more SR color image data and images from the sequence of subpixel shifted color frames and the motion vector using any suitable color SR techniques. For example, the simplest technique involves using the monochromatic SR technique on each of the color components independently. As another example, a more complicated SR technique can be used that involves transforming to a different color space, such as the one found in Farsiu, Sina, et al., "*Advances and challenges in super-resolution*," Wiley Periodicals (2004).

Scheme 3—Computed Color Two-Dimensional SROFM

In a third scheme, different wavelengths of light can be used to illuminate the sample at different points in time, generating several sequences of LR frames, each with a different wavelength or color of light. The resulting HR images could then be combined to compute a color HR image data and image of the object(s) being imaged. The wavelengths of light can be chosen to cover the widest viewable color range.

In this scheme, different wavelengths of light or colors of light sequentially illuminate the fluid specimen during a series of sampling times. By providing different wavelengths or colors of light in sequence, the light detector 122 can sample sequences of LR frames, each sequence associated with a different wavelength or color. In one embodiment, different illumination sources may be used to generate different wavelengths or colors of light. During operation, the illumination sources may be switched on and off, one after another (sequentially) during sampling. A sequence of frames sampled at times when an illumination source is switched on can be used to reconstruct, with an SR algorithm, an HR image of the wavelength or color associated with the corresponding illumination source. In this way, the SROFM can reconstruct HR image data and HR image for each wavelength or color. The SROFM 10 can combine the reconstructed HR images of different wavelengths or colors to obtain a multi-color HR image.

In one embodiment, a SROFM 10 may use RGB illumination to sequentially illuminate the fluid specimen during a series of sampling times. RGB illumination refers to using three illumination sources (e.g., LEDs): a red light source, a green light source, and a blue light source. During operation, the three illumination sources can be switched on and off, one after another (sequentially) during sampling. In this example, every third sampling time, the light detector 122 would sample a frame of a light projection from one of the three illumination sources. A sequence of frames associated with a particular color can be sampled at times when an illumination source of a color is switched on. Each sequence of frames can be used to reconstruct, using an SR algorithm, an SR color image and image data of the color associated with the corresponding illumination source. In this way, the SROFM 10 can reconstruct an SR red image, an SR green image, and an SR blue image. The SROFM 10 can combine the three reconstructed HR images to obtain a multi-color HR image.

Figure 7:
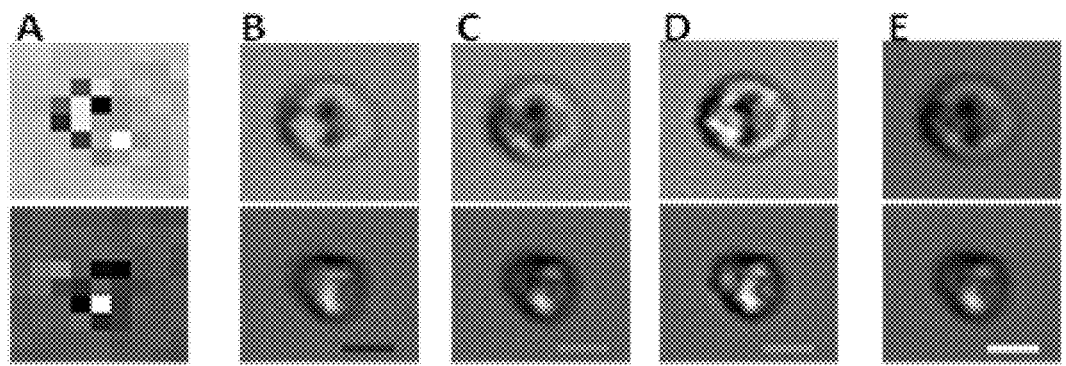
FIG. 7 includes images obtained with a SROFM using RGB illumination of two stained red blood cells with malaria infection, according to an embodiment of the invention.

For example, a SROFM 10 using RGB illumination can be used to reconstruct a color HR image of a stained red blood cell with malaria infection. FIG. 7 are images obtained with a SROFM 10 using RGB illumination of two stained red blood cells with malaria infection, according to an embodiment of the invention. FIG. 7(A) shows LR images of the stained red blood cells. FIGS. 7(B), 7(C), and 7(D) show three HR images (Red-B, Green-C, and Blue-D) obtained sequentially with three LED illumination sources. The SROFM 10 can combine the three HR images (Red-B, Green-C, and Blue-D) of each stained red blood cell to generate one color HR image.

Scheme 4—SROFM for Three-Dimensional Display

In a fourth scheme, the SR imaging concept is extended to three-dimensional imaging on a three-dimensional display 230. In this scheme, object 150 is imaged to obtain n two-dimensional HR images and corresponding image data from n different incidence angles, $\theta_1, \ldots \theta_n$. Any number n of incidence angles can be used (e.g., 2, 3, 4, etc.). In some cases, two or more of the n two-dimensional HR images at different incidence angles can be combined to form a three-dimensional HR image. The two-dimensional HR images and/or three-dimensional HR images generated by the SROFM 10 in this scheme can be displayed on a three-dimensional display (e.g., three-dimensional monitor).

In one case, one or more illumination sources provide light 140 from different incidence angles during sampling. In one example, the one or more illumination sources may cycle through light of different incidence angles from one frame to the next neighboring frame so that one or more sequences of projection, LR images are created. If more than one illumination source having more than one incidence angle are used, the illumination sources may be switched on and off, one after another (sequentially) during sampling. By providing light from multiple incidence angles sequentially, the light detector 122 can sample multiple sequences of LR frames, each sequence associated with a different incidence angle. In another example, the one or more illumination sources may provide light of a first incidence angle during a first series of sampling times, and then provide light of a second incidence angle during a second series of sampling times, and so forth until n sequences of frames corresponding to n different incidence angles have been sampled.

In a second case, the object(s) 150 being imaged may be rotated between the sampling of different sequences of frames.

After the sequences of frames have been sampled, the SROFM 10 can use an SR algorithm to reconstruct two-dimensional HR image data and images from different incidence angles. Each two-dimensional HR image data or image is reconstructed from a sequence of frames associated with a corresponding incidence angle. The SROFM 10 can combine two-dimensional HR images from different incidence angles to generate a three-dimensional HR image.

Figure 8:
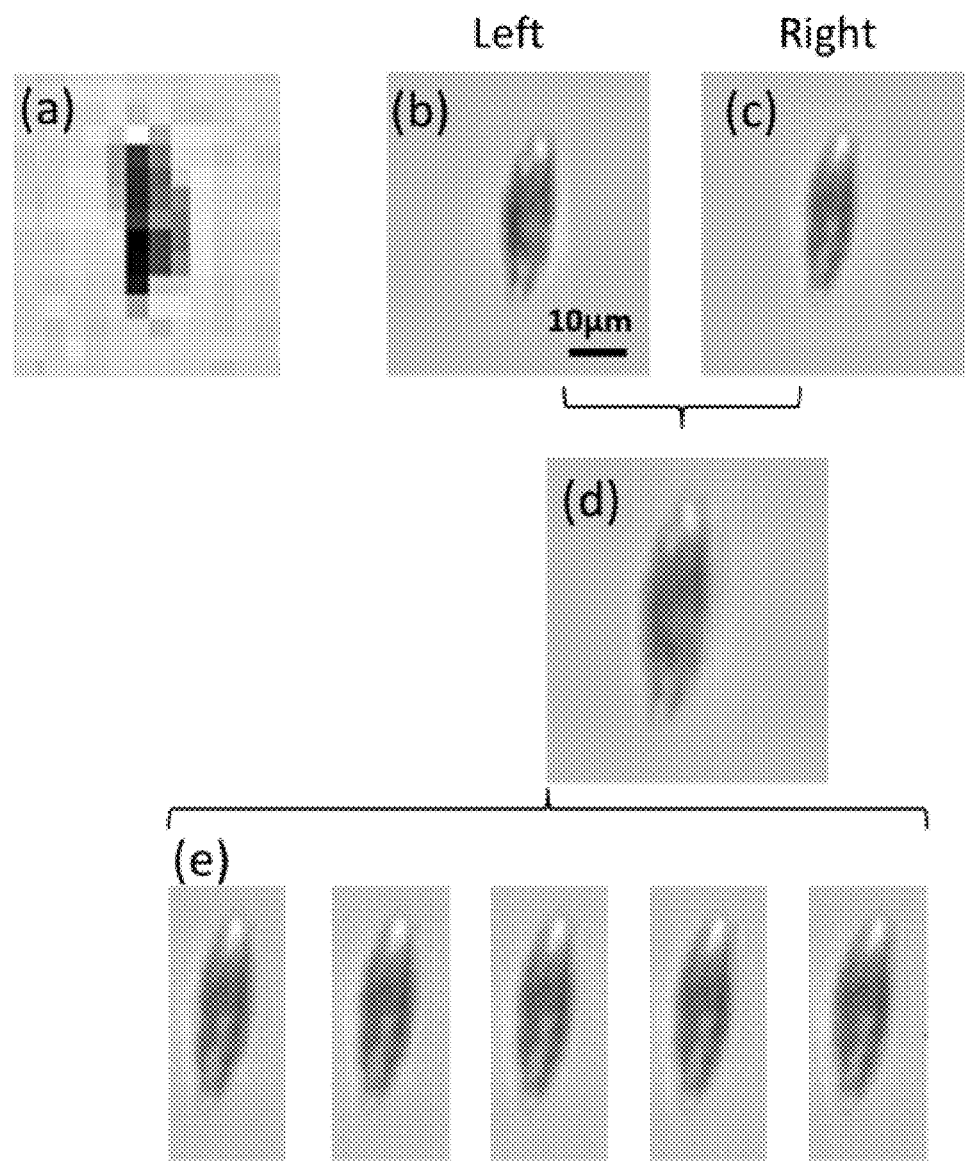
FIG. 8 includes images of a *Euglena gracilis* obtained with a SROFM based on light from different incidence angles, according to an embodiment of the invention.

FIG. 8 has images of a *Euglena gracilis* obtained using a SROFM 10 based on light from different incidence angles, according to an embodiment of the invention. FIG. 8(a) is a first LR frame of the *Euglena gracilis* sampled by the SROFM 10, according to an embodiment of the invention. This first LR frame is the first in a sequence of frames associated with a left projection. FIG. 8(b) is a reconstructed left projection SR two-dimensional image of the *Euglena gracilis*, obtained by the SROFM 10, according to an embodiment of the invention. FIG. 8(c) is a reconstructed right projection SR two-dimensional image of the *Euglena gracilis*, obtained by the SROFM 10, according to an embodiment of the invention. FIG. 8(d) is a three-dimensional HR image of the *Euglena gracilis* obtained by the SROFM 10, according to an embodiment of the invention. The three-dimensional HR image shown in FIG. 8(d) is a red-cyan anaglyph image generated by combining the reconstructed left projection SR two-dimensional image shown in FIG. 8(b) with the reconstructed right projection SR two-dimensional image shown in FIG. 8(c). FIG. 8(e) are interpolated images from FIGS. 8(b) and 8(c) to show multiple viewing angles used in FIGS. 8(b) and 8(c).

Scheme 5—Three-Dimensional SROFM with Computed Tomography

In a fifth scheme, the SR imaging concept is extended for three-dimensional imaging with computed tomography. In this scheme, the incident light 140 can be adjusted to n different incidence angles, $\theta_1, \ldots \theta_n$. Each incidence angle provides a different projection and view of the object 150. The light detector 122 samples a sequence of frames at each incidence angle.

In this fifth scheme, one or more illumination sources can be used to provide incident light 140 from different incidence angles. In some embodiments, the one or more illumination sources may cycle through light of different incidence angles from one frame to the next frame so that different sequences of projection, LR frames are obtained by the light detector 122. If multiple illumination sources are used, the illumination sources may be switched on and off, one after another (sequentially) during sampling. In one exemplary embodiment of the simplest case of obtaining two HR images of the same object 150 but from different angles, two different projection illumination sources can be alternated for neighboring frames so that two LR frame sequences are created. In other embodiments, the one or more illumination sources may provide light of a first incidence angle during a first series of sampling times, and then provide light of a second incidence angle during a second series of sampling times, and so forth until n sequences of frames corresponding to n different incidence angles have been sampled.

Figure 9:
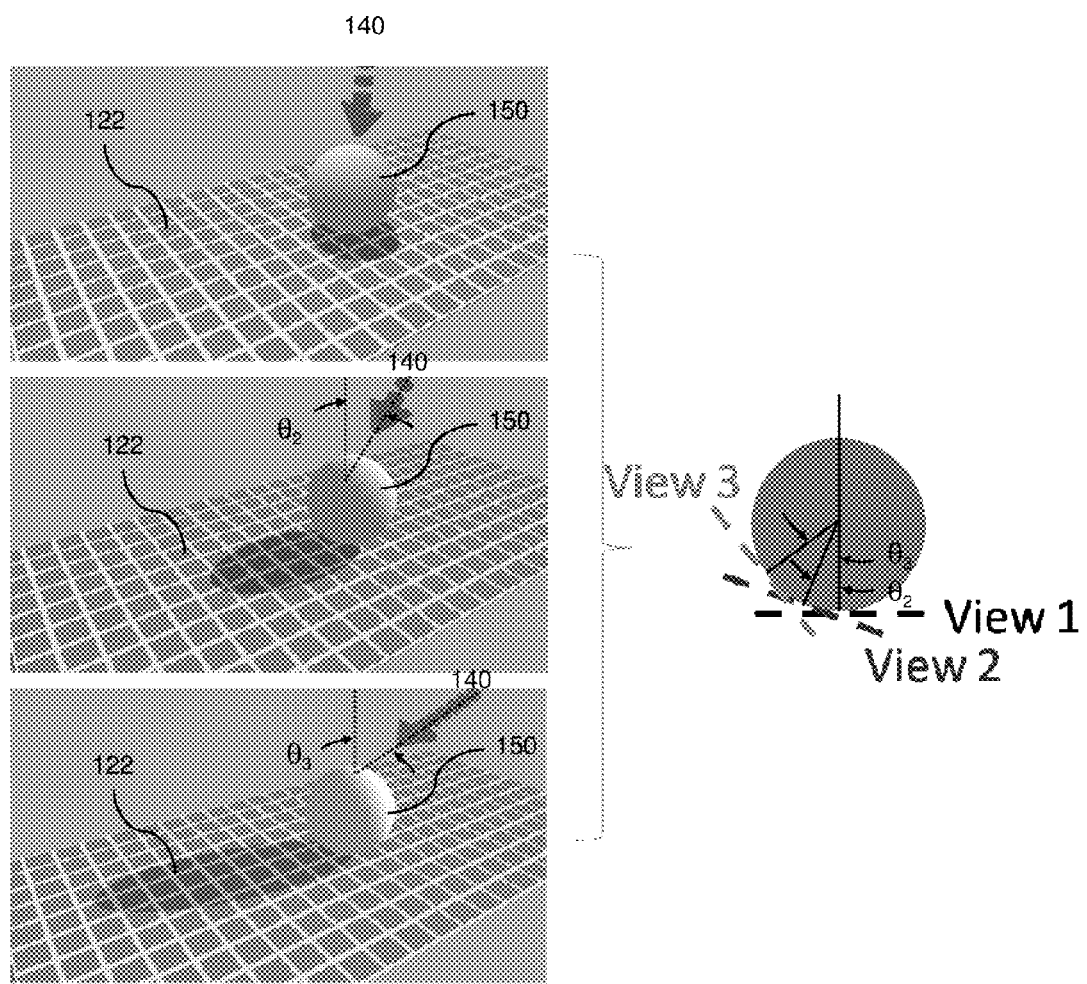
FIG. 9 is a schematic drawing of three projections on a light detector from three different incidence angles, $\theta_1$, $\theta_2$, and $\theta_3$, according to an embodiment of the invention.

FIG. 9 is a schematic drawing of three projections on a light detector 122 from three different incidence angles, $\theta_1$, $\theta_2$, and $\theta_3$, according to an embodiment of the invention. Changing the incident angle of the light 140 from the illumination source provides different views of the object 150. FIG. 9 shows a schematic representation of three different views, View 1, View 2, and View 3 associated respectively with the three different incidence angles $\theta_1$, $\theta_2$, and $\theta_3$. In FIG. 9, $\theta_1=0$ degrees, and is in the direction of a negative z-axis.

In other embodiments, the object(s) 150 being imaged may be rotated between the sampling of different sequences of frames. In these embodiments, the illumination source(s) remain stationary.

After sampling a sequence of frames for each incidence angle, the SROFM 10 can generate two-dimensional HR images for the different incidence angles. Then, the SROFM 10 can generate a three-dimensional HR image using a tomography algorithm from two or more of the generated two-dimensional HR images.

IV. Diagnostic Applications

In diagnostic applications, embodiments of a SROFM 10 can be used for diagnosing conditions and diseases such as malaria, sickle cell anemia, bacterial infection, etc. In these applications, the SROFM 10 can use its color capability for SR color imaging of stained objects such as cells, and bacteria and other microscopic organisms. In one such embodiment, for example, three illumination sources can be used: a red illumination source, a green illumination source, and a blue illumination source. These illumination sources may be provided by LEDs in some cases. During operation, the three illumination sources are switched on one after another (sequentially) during sampling. A sequence of frames sampled at times when a particular illumination source is switched on can be used to reconstruct an HR image of the corresponding color. In this way, the SROFM 10 can reconstruct an HR image for each color: red, green, and blue. For example, a sequence of frames sampled at every third sampling time can be used to reconstruct an HR image for each corresponding color. The SROFM 10 can combine the three HR images to obtain a final color HR image of the stained object(s). In another embodiment, a color light detector can be used to generate a color HR image.

Using reconstructed SR color images of the stained object(s) obtained by the SROFM 10, a user or the processor 210 can diagnose conditions and disease by identifying cells with atypical morphology or color, or pathogens. For example, the processor 210 may use code with an image recognition algorithm to identify pathogens or cells with atypical morphology or color. The processor 210 can then diagnose the conditions and disease based on the identification.

Malaria is an example of a disease that can be diagnosed with a SROFM 10. Malaria is responsible for millions of deaths each year, with an estimated 400 million to 600 million cases annually. Developing inexpensive malaria diagnostic techniques is a crucial step towards combating this epidemic, especially in developing countries.

The conventional method for imaging-based malaria diagnosis involves preparing a film of blood on a glass slide, which usually takes 10 to 15 minutes between sample collection and imaging. Since SROFMs 10 utilize a sample in a liquid format (i.e. fluid specimen), this preparation step can be significantly simplified to as simple as mixing a drop of blood into a prepared solution of reagents including anti-coagulant, buffer and staining solution.

In the diagnostics protocol of a SROFM 10 used for malaria diagnostics, the fluid specimen is prepared using an in-solution staining protocol of malaria parasites using Toluidine Blue stain. This staining only highlights the parasites in dark purple and renders the red blood cells in pinkish color. In this way, the parasites in the blood cells can be identified and the parasitemia of the patient can be qualified. The reagent mixture can be further optimized to provide adequate blood-cell concentration and high-contrast staining for the parasite identification.

In one such application for diagnosing malaria, the SROFM 10 uses its color capability for SR imaging of stained red blood cells to determine whether the red blood cells have a malaria-infected parasite. In these embodiments, three illumination sources are used: a red illumination source, a green illumination source, and a blue illumination source. These illumination sources may be provided by LEDs in some cases. During operation, the three illumination sources are switched on one after another (sequentially) during sampling. A sequence of frames sampled at times when a particular illumination source is switched on can be used to reconstruct an HR image of the corresponding color. In this way, the SROFM 10 can reconstruct an HR image for each color: red, green, and blue. For example, a sequence of frames sampled at every third sampling time can be used to reconstruct an HR image for each corresponding color. The SROFM 10 can combine the three HR images to obtain a final color HR image of the stained red blood cell.

FIG. 10(a) is a schematic drawing of a malaria diagnostics-based SROFM 10, according to an embodiment of the invention. In FIG. 10(a), the SROFM 10 includes a body 110 having a micromolded PDMS microfluidic chip coupled directly to a light detector 122 (e.g., a CMOS sensor). The fluid channel 112 includes an inlet 160 and an outlet 170 connected to opposite ends of the fluid channel 112. The light detector 112 includes light detecting elements 124 in the form of a two-dimensional array. In FIG. 10(a), the red blood cells being imaged move through the fluid channel 112 in the microfluidic chip.

In this embodiment, red, green and blue illumination sources (e.g., LED) provide light 140 (light having wavelengths associated with red, green, blue colors) to the fluid channel 112 creating projection images on the light detector. These three illumination sources are switched on one after another (sequentially) during sampling, and thus, the SROFM 10 can reconstruct an HR image for each color (red, green, blue). The SROFM 10 can combine the three HR images to obtain a final color image of the stained red blood cell.

To use the malaria diagnostics-based SROFM 10 for malaria diagnostics, a drop of blood sample mixture can be injected into the SROFM 10 and flowed through the fluid channel 112. The volume of a fluid specimen having objects 150 being imaged in a malaria diagnostics-based SROFM 10 in one embodiment is about 1-2 micro liters at the flow rate of 0.5-1 mm/sec. In some cases, the flow is induced by the combination of capillary effect and the pressure difference between the inlet 160 and the outlet 170 of the SROFM 10. In one case, the SROFM 10 may provide a drop-and-flow scheme with blood samples with the flow rate of 1 mm/sec. At this rate, the achievable throughput would be up to 5000 cells per minute, which corresponds to the detection yield of 0.002% parasitemia in 10 minutes. Current commercial kits range from 0.002%~0.1% parasitemia in 20 minutes.

FIG. 10(b) shows reconstructed HR images of the malaria-infected red blood cells obtained by the SROFM 10 of FIG. 10(a), according to an embodiment of the invention. FIG. 10(c) shows reconstructed HR images of non-infected red blood cells obtained by the SROFM 10 of FIG. 10(a), according to an embodiment of the invention. The purple (dark) regions of the red blood cell images in FIG. 10(b) indicate the malaria-infected parasite. Using the reconstructed HR images obtained by the SROFM 10, a user or the processor 210 can identify parasites within the red blood cells and distinguish infected and non-infected red blood cells. In some cases, the user can diagnose malaria based on the results. Alternatively, the processor 210 may use code with a malaria diagnosis algorithm including an image recognition algorithm to identify the parasites, distinguish infected and non-infected red blood cells, and/or diagnose malaria.

V. Flow Chart of Imaging Process

Figure 11:
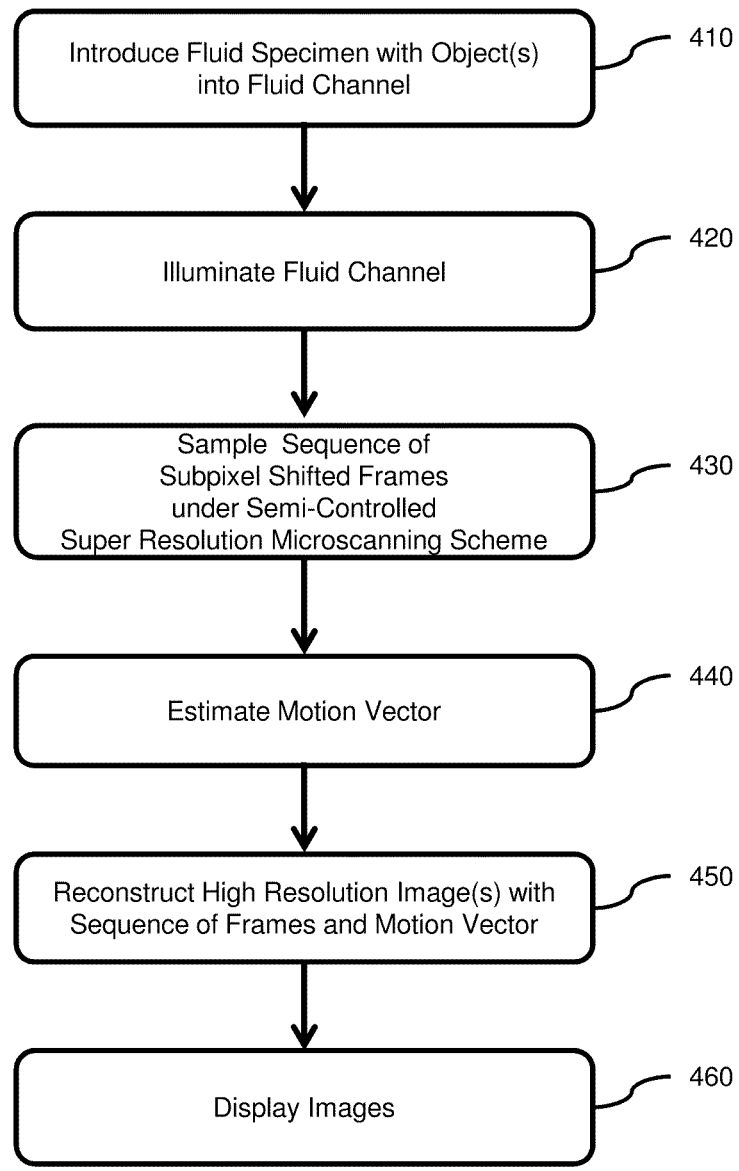
FIG. 11 is a flow chart of the operation of the SROFM, according to embodiments of the invention.

FIG. 11 is a flow chart of the operation of the SROFM 10, according to embodiments of the invention. In step 410, a fluid specimen with object(s) 150 being imaged is introduced into the fluid channel 112. In one embodiment, the fluid specimen may be introduced through an inlet 160 (shown in FIG. 2(a)) in the fluid channel 112. If more than one object 150 is being imaged, the fluid specimen may contain an adequate concentration of target objects 150.

A fluid flow that carries the fluid specimen with the object(s) 150 being imaged through the fluid channel 112 and across the two-dimensional array of light detecting elements 124 in the general direction of the longitudinal axis of the fluid channel 112. Any suitable technique of fluid flow and/or particulate transport can be used to move the object(s) 150 through the fluid channel 112. Some convention techniques include pressure drive flow, electrokinetic transport, discrete droplet translocation via electrowetting, or thermocapilarity techniques. Other techniques may include gravity drive flow, hydrodynamic focusing, dielectrophoresis, and optical tweezing. In one embodiment, a fluid flow may be induced by the capillary action and the pressure difference between the inlet 160 and outlet 170, delivering the objects 150 through the imaging area above the two-dimensional array of light detecting elements 124 of the light detector (e.g., CMOS sensor).

In some embodiments, a control device(s) may be used to control the flow of fluid and/or movement of the object 150 through the fluid channel 112. Some examples of suitable control devices include micropumps, direct current (DC) electrokinetic devices, dielectrophoresis electrodes, and/or hydrodynamic focusing channels.

In some cases, the channel height of the fluid channel 112 is sized to keep the object(s) 150 being imaged close to the first surface layer 120, which may help improve the quality of imaged generated by the SROFM 10.

In step 420, one or more illumination sources provide incident light 140 to illuminate the fluid channel 112. In some embodiments, incident light 140 at multiple incidence angles and/or multiple wavelengths may be provided by the one or more illumination sources.

Figure 10:
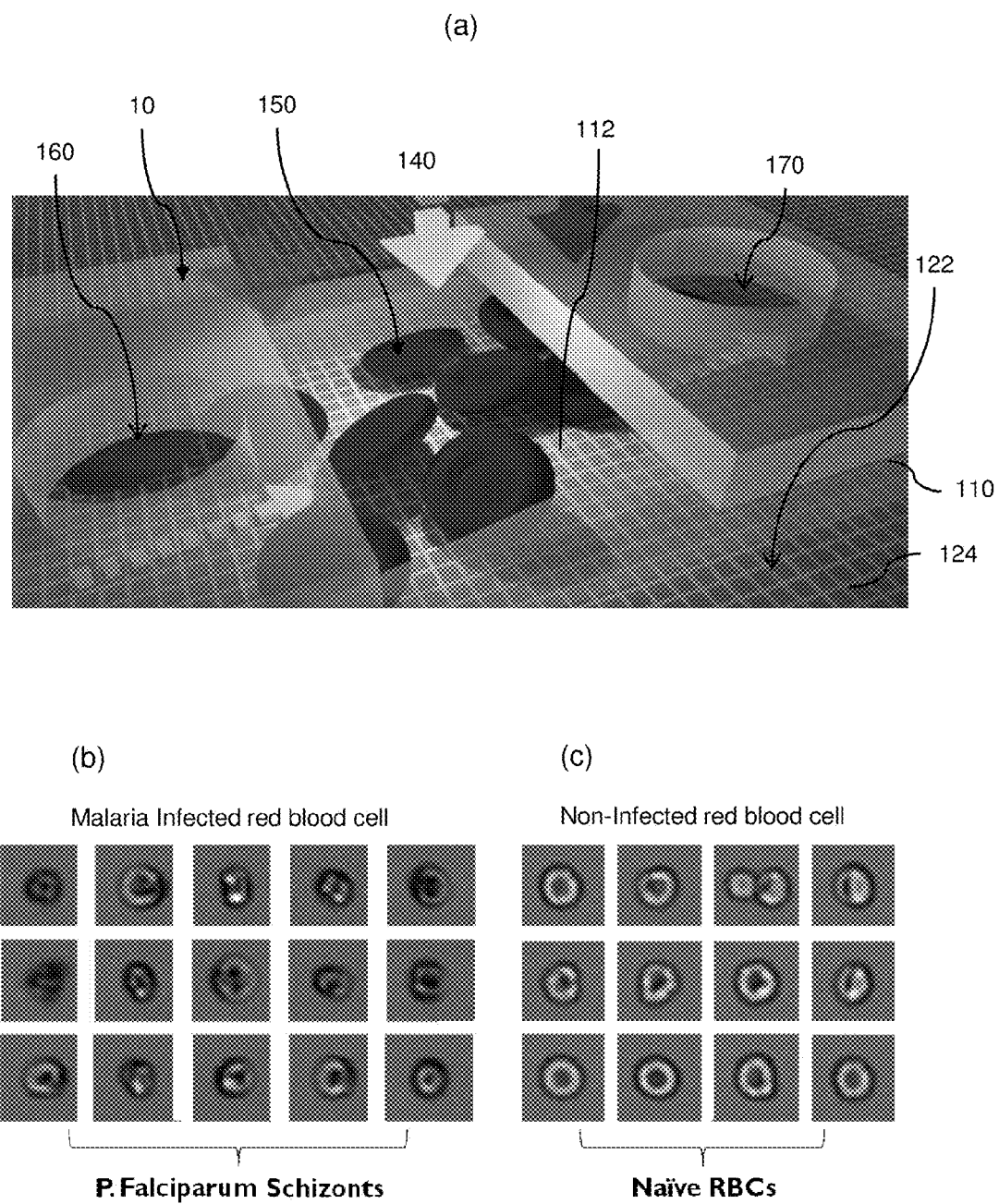
FIG. 10(a) is a schematic drawing of a malaria diagnostics-based SROFM, according to an embodiment of the invention.
FIG. 10(b) includes reconstructed HR images of the malaria-infected red blood cells obtained by the SROFM of FIG. 10(a), according to an embodiment of the invention.
FIG. 10(c) includes reconstructed HR images of non-infected red blood cells obtained by the SROFM of FIG. 10(a), according to an embodiment of the invention.

In three-dimensional imaging embodiments, for example, illumination source(s) may provide light of different incidence angles at different sampling times to generate a different sequence of frames for each incidence angle. Changing the incidence angle provides different views of the object(s) being imaged. An example of three different views of an object 150 based on three different incidence angles $\theta_1$, $\theta_2$, and $\theta_3$ is shown in FIG. 10. In some cases, illumination source(s) providing light of different incidence angles may be switched on and off, one after another (sequentially) during sampling. In other cases, illumination source(s) may provide light of a first incidence angle during a first series of sampling times, and then provide light of a second incidence angle during a second series of sampling times, and so forth until n sequences of frames corresponding to n different incidence angles have been sampled. Alternatively, the object(s) 150 being imaged may be rotated between the sampling of different sequences of frames while illumination source(s) remains stationary.

In some embodiments, the illumination source can provide light 140 of n different wavelengths $\lambda_1, \ldots, \lambda_n$ at different times during sampling to obtain a sequence of frames for each wavelength. Any suitable number of wavelengths may be used (e.g., n=1, 2, 3, 4, 5, . . . , 20). In one embodiment, a SROFM 10 with RGB illumination provides incident light 140 of three wavelengths $\lambda_1$, $\lambda_2$, and $\lambda_3$ corresponding to red, green, blue colors at different sampling times. In some cases, the illumination source(s) may be switched on and off, from one frame to a neighboring frame, sequentially during sampling. In other cases, illumination source(s) may provide light of a first wavelength during a first series of sampling times, and then provide light of a second wavelength during a second series of sampling times, and so forth until n sequences of frames corresponding to n different wavelengths have been sampled.

In step 430, the light detector 122 samples one or more sequences of subpixel shifted frames as the object(s) 150 being imaged move through the fluid channel 112 with the fluid flow. Each frame includes two-dimensional light data that can be used to display a two-dimensional LR image of the object(s) 150. Any flow rate, subpixel sampling rate, and field-of-view (FOV) can be used that will generate a suitable sequence of subpixel shifted frames for reconstructing a HR image using a SR algorithm. In one example, object(s) 150 were imaged at a flow rate of 200 µm/s, and the light detector 122 had a subpixel sampling rate of 500 fps and a field-of-view (FOV) of 250 µm by 3 mm. The flow rate of the fluid specimen, and hence throughput, can be increased with a smaller FOV and higher subpixel sampling rate. In one example, 50 LR frames were enough to generate a reconstructed HR image with a resolution enhancement factor of 7 indicating that with the Aptina Inc.® MT9M001C12STM CMOS sensor's maximum frame sampling rate of 50000 fps and FOV of 50 µm by 100 µm, a continuous stream of objects 150 can be imaged at a rate of 1000 images/sec, with each image possibly containing multiple objects 150.

In many embodiments, the semi-controlled subpixel movement of the object(s) 150 between frames captured by the light detector 122 may allow for accurate reconstruction of HR images of microscopic object(s) from the sequence of LR frames sampled by the light detector 122 including sparsely populated light detectors. The subpixel movement can be semi-controlled by the geometry of the fluid channel 122, the control of the fluid flow, and/or the control of the movement of the object(s).

In step 440, the processor 210 uses any suitable method of calculating a motion vector of the object(s) 150 being imaged. In many embodiments, the motion vector can be easily analyzed and accurately determined because the flow rate is highly stable within the fluid channel 112 (i.e. low Reynolds number) used with the semi-controlled SR microscanning scheme of the SROFM 10. For object(s) 150 moving at constant speed, the motion vector can be calculated from the location of the object(s) 150 in the first and last frames. In cases where the motion of the object(s) 150 is not uniform, a motion vector estimation algorithm can be used.

In one motion vector estimation algorithm, first the background of each LR frame is subtracted and the contrast enhanced. Highly scattering objects in LR frames appear darker than the background, thus this information can be used to determine the location of the object within each LR frame. To do this, the frame is binarized using a single threshold computed from the entropy of the image histogram. An example of binarizing a frame can be found in Kapur, J., et al., Computer vision, graphics, and image processing, 29, pp. 273-285 (1985). The geometric centroid of each of these binarized frames from the LR frame sequence is then computed and the entire array of centroids is low pass filtered to account for both the smooth flow pattern of the fluid specimen and the quantization error from binarizing and computing the centroid of each individual LR frame.

For samples with lower contrast or bright spots, the motion vector is calculated in a similar manner, except the frames are binarized with two thresholds. The background noise level is calculated and the frame binarized by converting any pixel that is a certain amount above or below the noise level to 0 while making the rest 1. Also, in order to avoid errors due to the geometry of the object 150, the algorithm uses the pixel coordinate of the bounding box of the object 150 and low pass filter the data to obtain sub-pixel shift values. For objects 150 (e.g., microspheres) that are smaller than a pixel size, it is more difficult to distinguish a pixel response that results from the shadowing of the object 150 from the light detector's background noise. In this case, the motion vector is obtained by observing the blinking of the pixels on the expected pathway of objects 150 (parallel to the channel wall). From the raw data, the pixel coordinates are obtained where the objects 150 are expected to flow through. This pathway can be any line of pixels within the fluid channel 112 that are parallel to the channel wall, since the objects 150 follow the laminar flow of the solution. The algorithm extracts the time variation of the pixel response on the pathway, which shows the blinking of the pixels as the object 150 moves across each pixel, and calculate the motion vector from the slope ($\Delta x/\Delta f$, $\Delta y/\Delta f$).

In step 450, the processor 210 uses an appropriate SR algorithm to reconstruct one or more two-dimensional reconstructed HR images from each sequence of frames and corresponding motion vector. Each frame can be considered a subsampled version of the original image, with the sampling rate corresponding to a pixel size. If the light detector 122 is a monochromatic light detector, the image resulting from this reconstruction is a black and white image. If the light detector 122 is a color light detector (e.g., a color CMOS sensor), the image resulting from this reconstruction is a color image.

In one embodiment, a shift-and-add SR algorithm is used to reconstruct an HR image from a sequence of subpixel shifted frames. In this embodiment, an HR image grid is formed with an enhancement factor of n, where each n-by-n pixel area of the HR image grid corresponds to a 1-by-1 pixel area of the LR frame grid. Then, the HR image grid is filled with the corresponding pixel values from the sequence of subpixel shifted frames. The mapping of the pixels within the n-by-n grid is determined from the known, estimated sub-pixel shift of each image from the motion vector estimated using the motion vector estimation algorithm. In other words, each frame is shifted by the relative sub-pixel shift of the object from its original position and then added together to form a HR image. Finally, deblurring using the wiener deconvolution method is used to remove blurring and noise in the final HR image.

In an embodiment where the one or more illumination sources provide light 140 of n different wavelengths $\lambda_1, \ldots, \lambda_n$ at different times during sampling to obtain a sequence of frames for each wavelength, the processor 210 can use an appropriate SR algorithm to reconstruct an HR image for each wavelength or color based on each sequence of frames and the motion vector. The SROFM 10 can combine the HR images of different wavelengths or colors to obtain a computed multi-color HR image. For example, a SROFM 10 using RGB illumination from can be used to construct a computed multi-color (RGB) HR image.

In a three-dimensional imaging embodiment with computed tomography where the one or more illumination source(s) provide light of different incidence angles $\theta_1, \ldots \theta_n$ at different sampling times to generate a sequence of frames for each incidence angle, the processor 210 can use an appropriate SR algorithm to reconstruct an HR image for each incidence angle using the sequence of frames and the motion vector. The processor 210 can generate a three-dimensional HR image using a tomography algorithm from two or more of the generated two-dimensional HR images based on different incidence angles.

In step 460, the processor 210 can display one or more images to a suitable display 230 (e.g., two-dimensional display (color or black and white), three-dimensional display (color or black and white)). Any suitable images generated by the SROFM 10 may be displayed. Some examples of suitable images include: one or more LR images from the sequence of LR frames may be displayed, one or more two-dimensional black and white HR images at one or more incidence angles, one or more two-dimensional color HR images based on using a color light detector, one or more two-dimensional multi-color HR images based on multiple wavelengths of incident light, one or more three-dimensional HR images based on combining two-dimensional SR images from two or more incidence angles on a three-dimensional display, and/or one or more three-dimensional HR images computed using a tomography algorithm from two or more two-dimensional HR images.

VI. Subsystems

Figure 12:
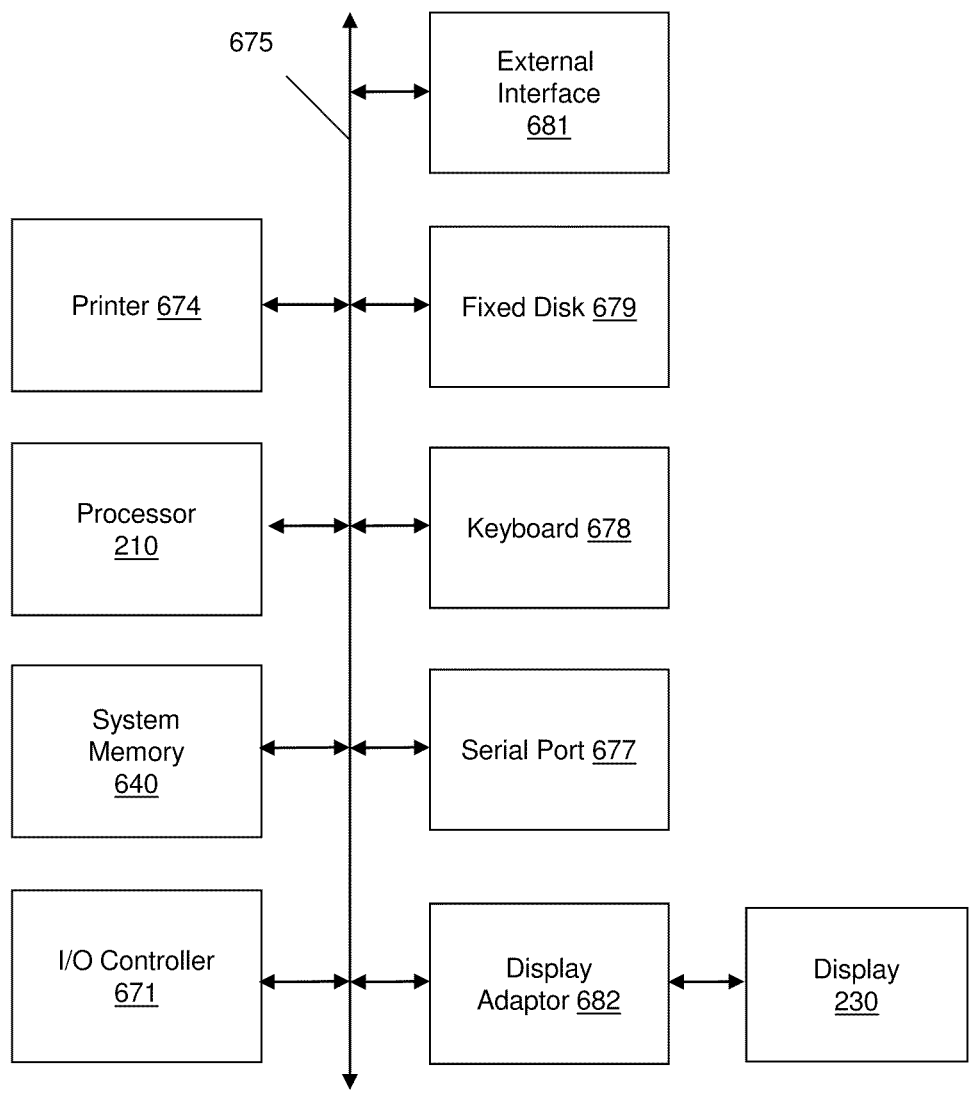
FIG. 12 is a block diagram of subsystems that may be present in the SROFM, according to embodiments of the invention.

FIG. 12 is a block diagram of subsystems that may be present in the SROFM 10, according to embodiments of the invention. For example, the SROFM 10 includes a processor 210 for processing light data and for generating two-dimensional and three-dimensional HR images of the object 130. The processor 210 may be a component of the light detector 122, in some cases.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 12. The subsystems shown in FIG. 12 are interconnected via a system bus 675. Additional subsystems such as a printer 674, keyboard 678, fixed disk 679 (or other memory comprising computer readable media), display 230, which is coupled to display adapter 682, and others are shown. Peripherals and input/output (I/O) devices, which couple to I/O controller 671, can be connected to the computer system by any number of means known in the art, such as serial port 677. For example, serial port 677 or external interface 681 can be used to connect the computer apparatus to a wide area network such as the Internet, a mouse input device, or a scanner. The interconnection via system bus allows the processor 210 to communicate with each subsystem and to control the execution of instructions from system memory 640 or the fixed disk 679, as well as the exchange of information between subsystems. The system memory 640 and/or the fixed disk 679 may embody a computer readable medium 220. Any of these elements may be present in the previously described features. A computer readable medium 220 according to an embodiment of the invention may comprise code for performing any of the functions described above.

In some embodiments, an output device such as the printer 674 or display 230 of the SROFM 10 can output various forms of data. For example, the SROFM 10 can output a two-dimensional image or a three-dimensional image of the object 130 or other results of analysis.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. A super resolution optofluidic microscope device, comprising:
   a multi-layer body comprising a micromolded microfluidic chip fabricated using micro/nanofabrication procedures, the micromolded microfluidic chip defining a fluid channel having a longitudinal axis;
   an image sensor, wherein the micromolded microfluidic chip is affixed directly to the image sensor during fabrication such that the image sensor is oriented with its local axis at an angle from the longitudinal axis of the fluid channel, wherein during operation the image sensor receives light passing through an object being imaged while the object is moving through the fluid channel and samples a sequence of subpixel shifted two-dimensional projection images of the object as it moves through the fluid channel; and
   a processor in electronic communication with the image sensor to receive data during operation that comprises the sampled sequence of subpixel shifted two-dimensional projection images of the object, wherein during operation the processor generates a high resolution two-dimensional image of the object from the sampled sequence of subpixel shifted two-dimensional projection images and a motion vector of the object using a super resolution algorithm.

2. The super resolution optofluidic microscope device of claim 1, wherein during operation the processor also executes code with a motion vector estimation algorithm to estimate the motion vector of the object moving through the fluid channel from the sequence of subpixel shifted two-dimensional projection images using a motion vector estimation algorithm.

3. The super resolution optofluidic microscope device of claim 1, wherein the fluid channel and the image sensor are configured to maintain semi-controlled movement of the object in subpixel shifts between sample times of the neighboring two-dimensional images in the sequence of subpixel shifted two-dimensional projection images.

4. The super resolution optofluidic microscope device of claim 1, wherein the angle is between 10 and 30 degrees.

5. The super resolution optofluidic microscope device of claim 1, wherein the subpixel shifted two-dimensional projection images are sampled at a subpixel sampling rate.

6. The super resolution optofluidic microscope device of claim 1, wherein the micromolded microfluidic chip further comprises:
   an inlet that receives a fluid specimen with the object into the fluid channel; and
   an outlet from which the fluid specimen exits the fluid channel.

7. The super resolution optofluidic microscope device of claim 1,
   wherein the image sensor is a color sensor array, and
   wherein the high resolution image is a color image.

8. The super resolution optofluidic microscope device of claim 1, wherein the image sensor is a CMOS sensor chip.

9. A super resolution optofluidic microscope device, comprising:
   a multi-layer body comprising a micromolded microfluidic chip fabricated using micro/nanofabrication procedures, the micromolded microfluidic chip defining a fluid channel having a longitudinal axis; and
   an image sensor, wherein the micromolded microfluidic chip is affixed directly to the image sensor during fabrication such that the image sensor is oriented with its local axis at an angle from the longitudinal axis of the fluid channel, and wherein during operation the image sensor receives light of different wavelengths passing through an object being imaged while the object is moving through the fluid channel and samples a plurality of sequences of subpixel shifted two-dimensional projection images of the object as it moves through the fluid channel, wherein each sequence is associated with a different wavelength band corresponding to a color.

10. The super resolution optofluidic microscope device of claim 9, further comprising a processor in electronic communication with the image sensor, the processor configured to generate a plurality of high resolution two-dimensional images associated with the different wavelengths based on data received from the image sensor during operation comprising the plurality of sequences of subpixel shifted projection two-dimensional images, wherein the plurality of high resolution two-dimensional images is generated using a super resolution algorithm from the plurality of sequences of subpixel shifted projection two-dimensional images and a motion vector.

11. The super resolution optofluidic microscope device of claim 10, wherein during operation the processor also combines the plurality of high resolution two-dimensional images based on the different wavelengths of multiple colors to form a multi-color, high resolution image of the object.

12. The super resolution optofluidic microscope device of claim 11, wherein during operation the processor also executes code with an image recognition algorithm to identify conditions or disease from the multi-color high resolution image of the object.

13. The super resolution optofluidic microscope device of claim 10, wherein during operation the processor also executes code with a motion vector estimation algorithm to estimate the motion vector of the object moving through the fluid channel from at least one sequence of subpixel shifted projection two-dimensional images using a motion vector estimation algorithm.

14. The super resolution optofluidic microscope device of claim 9, wherein the angle is between 10 and 30 degrees.

15. The super resolution optofluidic microscope device of claim 9, wherein the different wavelengths comprise three wavelengths bands corresponding to a blue color, a red color, and a green color.

16. The super resolution optofluidic microscope device of claim 9, wherein the light of different wavelengths is provided sequentially to the object being imaged, wherein light of each wavelength is provided by one of a plurality of illumination sources.

17. A super resolution optofluidic microscope device, comprising:
  a multi-layer body comprising a micromolded microfluidic chip fabricated using micro/nanofabrication procedures, the micromolded microfluidic chip defining a fluid channel having a longitudinal axis; and
  an image sensor, wherein the micromolded microfluidic chip is affixed directly to the image sensor during fabrication such that the image sensor is oriented with its local axis at an angle from the longitudinal axis of the fluid channel, and wherein during operation the image sensor receives light of different incidence angles passing through an object being imaged while the object is moving through the fluid channel, and samples a plurality of sequences of subpixel shifted two-dimensional projection images of the object as it moves through the fluid channel, wherein each sequence is associated with a different incidence angle.

18. The super resolution optofluidic microscope device of claim 17, further comprising a processor in electronic communication with the image sensor, the processor configured to generate a plurality of high resolution two-dimensional images associated with the different incidence angles based on data received from the image sensor during operation comprising the plurality of sequences of subpixel shifted projection two-dimensional images, wherein the plurality of high resolution two-dimensional images is generated using a super resolution algorithm from the plurality of sequences of subpixel shifted projection two-dimensional images and a motion vector.

19. The super resolution optofluidic microscope device of claim 17, wherein during operation the processor also combines the plurality of high resolution images based on the different incidence angles to form a three-dimensional high resolution image of the object.

20. The super resolution optofluidic microscope device of claim 19, wherein the plurality of high resolution images are combined by executing code with a tomography algorithm.

21. The super resolution optofluidic microscope device of claim 18, wherein during operation the processor also executes code with a motion vector estimation algorithm to estimate the motion vector of the object moving through the fluid channel from at least one sequence of subpixel shifted projection two-dimensional images using a motion vector estimation algorithm.

22. The super resolution optofluidic microscope device of claim 17, wherein the angle is between 10 and 30 degrees.

23. The super resolution optofluidic microscope device of claim 17, wherein the light of the different incidence angles is provided sequentially to the object being imaged, wherein light of each of the different incidence angles is provided by one of a plurality of illumination sources.

24. A super resolution optofluidic microscope device, comprising:
  a multi-layer body comprising a micromolded microfluidic chip fabricated using micro/nanofabrication procedures, the micromolded microfluidic chip defining a fluid channel having a longitudinal axis;
  a complementary metal-oxide-semiconductor/CMOS) sensor, wherein the micromolded microfluidic chip is affixed directly to the CMOS sensor during fabrication such that the CMOS sensor is oriented with its local axis at an angle from the longitudinal axis of the fluid channel, and wherein during operation the CMOS sensor receives light passing through an object being imaged while the object is moving through the fluid channel and samples a sequence of subpixel shifted two-dimensional projection images of the object as it moves through the fluid channel; and
  a mobile communication device having a processor and a display, the processor in electronic communication with the CMOS sensor to receive data during operation that comprises the sampled sequence of subpixel shifted two-dimensional projection images of the object, wherein during operation the processor generates a high resolution two-dimensional image of the object with the sampled sequence of subpixel shifted projection two-dimensional images and a motion vector using a super resolution algorithm, the processor further configured to display the high resolution image on the display.

25. The super resolution optofluidic microscope device of claim 24, wherein the mobile communication device comprises a phone.

26. The super resolution optofluidic microscope device of claim 24, wherein during operation the processor also executes code with a motion vector estimation algorithm to estimate the motion vector of the object moving through the fluid channel from the sequence of subpixel shifted projection two-dimensional images.

27. A method of generating a high resolution image of an object using a super resolution optofluidic microscope device comprising a micromolded microfluidic chip defining a fluid channel, the micromolded microfluidic chip affixed directly to a complementary metal-oxide-semiconductor (CMOS) image sensor such that CMOS image sensor is oriented with its x-axis at an angle of between 10 and 30 degrees from the longitudinal axis of the fluid channel, the method comprising:
  illuminating the fluid channel;
  high speed sampling, by the CMOS image sensor, of a sequence of subpixel shifted two-dimensional projection images of the object as it moves through the fluid channel in both an x-direction along the x-axis and in a y-direction along the y-axis of the CMOS image sensor; and
  executing code with a super resolution algorithm, to reconstruct, using a processor, the high resolution image of the object from the sampled sequence of subpixel shifted two-dimensional projection images and a motion vector of the object moving through the fluid channel.

28. The method of generating a high resolution image of the object of claim 27, further comprising executing code with a motion vector estimation algorithm to estimate the motion vector of the object from the sequence of subpixel shifted two-dimensional images.

29. The method of generating the high resolution image of the object of claim 27, further comprising introducing a fluid specimen with the object being imaged into the fluid channel such that the object flows through the fluid channel.

30. A method of generating a three-dimensional high resolution image of an object using a super resolution optofluidic microscope device comprising a micromolded microfluidic chip defining a fluid channel, the micromolded microfluidic chip affixed directly to an image sensor such that the image sensor is oriented with its x-axis at an angle of between 10 and 30 degrees from the longitudinal axis of the fluid channel, the method comprising:
  illuminating the fluid channel with light of different incidence angles to the object at different sampling times;
  high speed sampling, by the image sensor, a plurality of sequences of subpixel shifted two-dimensional projection images of the object as it moves through the fluid channel in both an x-direction along the x-axis and in a y-direction along a y-axis of the image sensor, each sequence associated with a different incidence angle;
  executing code with using a super resolution algorithm, using the processor, to reconstruct, a plurality of high resolution images of the object associated with different incidence angles from the plurality of sequences of subpixel shifted projection frames and a motion vector; and
  executing code with a tomography algorithm, using the processor, to combine the plurality of super-resolution images associated with different incident angles to generate the three-dimensional high resolution image of the object.

31. The method of generating the three-dimensional high resolution image of the object of claim 30, further comprising executing code with a motion vector estimation algorithm, using the processor, to estimate the motion vector of the object from at least one sequence of subpixel shifted images of the object.

32. The method of generating the three-dimensional high resolution image of the object of claim 30, wherein the image sensor is a CMOS image sensor.

33. The super resolution optofluidic microscope device of claim 1, wherein the micromolded microfluidic chip is bonded to a surface layer of the image sensor and the fluid channel has a height that maintains the object being imaged proximal the surface layer of the image sensor.

* * * * *